United States Patent
Abrol et al.

(10) Patent No.: US 12,217,417 B2
(45) Date of Patent: Feb. 4, 2025

(54) LEARNING-BASED DOMAIN TRANSFORMATION FOR MEDICAL IMAGES

(71) Applicants: GE Precision Healthcare LLC, Milwaukee, WI (US); University of Zurich, Zurich (CH)

(72) Inventors: Sidharth Abrol, Bangalore (IN); Bipul Das, Chennai (IN); Vanika Singhal, Bangalore (IN); Amy Deubig, Dousman, WI (US); Sandeep Dutta, Celebration, FL (US); Daphné Gerbaud, Buc (FR); Bianca Sintini, Issy-les-Moulineaux (FR); Ronny Büchel, Wangen bei Olten (CH); Philipp Kaufmann, Zurich (CH)

(73) Assignees: GE PRECISION HEALTHCARE LLC, Waukesha, WI (US); UNIVERSITY OF ZURICH, Zurich (CH)

( * ) Notice: Subject to any disclaimer, the term of this patent is extended or adjusted under 35 U.S.C. 154(b) by 674 days.

(21) Appl. No.: 17/470,076

(22) Filed: Sep. 9, 2021

(65) Prior Publication Data
US 2023/0071535 A1    Mar. 9, 2023

(51) Int. Cl.
*G06T 7/00* (2017.01)
*G06N 20/00* (2019.01)
(Continued)

(52) U.S. Cl.
CPC ........... *G06T 7/0012* (2013.01); *G06N 20/00* (2019.01); *G06T 5/70* (2024.01); *G06T 7/11* (2017.01);
(Continued)

(58) Field of Classification Search
USPC .................................................. 382/128–302
See application file for complete search history.

(56) References Cited

U.S. PATENT DOCUMENTS 9,189,832 B2   11/2015   Shechter
9,332,953 B2   5/2016    Suzuki
(Continued)

FOREIGN PATENT DOCUMENTS

CN    107403419 A    11/2017
CN    111182219 A    5/2020

OTHER PUBLICATIONS

Freiman Mordechay Pinchas; Apparatus for Generating Photon Counting Spectral Image Data; 2021 (Year: 2021).*
(Continued)

*Primary Examiner* — Marcellus J Augustin
(74) *Attorney, Agent, or Firm* — Amin, Turocy & Watson, LLP

(57) ABSTRACT

Systems/techniques that facilitate learning-based domain transformation for medical images are provided. In various embodiments, a system can access a medical image. In various aspects, the medical image can depict an anatomical structure according to a first medical scanning domain. In various instances, the system can generate, via execution of a machine learning model, a predicted image based on the medical image. In various aspects, the predicted image can depict the anatomical structure according to a second medical scanning domain that is different from the first medical scanning domain. In some cases, the first and second medical scanning domains can be first and second energy levels of a computed tomography (CT) scanning modality. In other cases, the first and second medical scanning domains can be first and second contrast phases of the CT scanning modality.

17 Claims, 13 Drawing Sheets

(51) Int. Cl.
*G06T 5/60* (2024.01)
*G06T 5/70* (2024.01)
*G06T 7/10* (2017.01)
*G06T 7/11* (2017.01)
*G06V 10/25* (2022.01)
*G16H 30/40* (2018.01)

(52) U.S. Cl.
CPC ............ *G06V 10/25* (2022.01); *G16H 30/40* (2018.01); *G06T 2207/10081* (2013.01); *G06T 2207/20081* (2013.01)

(56) References Cited

U.S. PATENT DOCUMENTS

| | | |
|---|---|---|
| 9,730,660 B2 | 8/2017 | Suzuki |
| 10,335,105 B2 | 7/2019 | Zhou |
| 2016/0210749 A1 | 7/2016 | Nguyen |
| 2019/0325621 A1 | 10/2019 | Wang et al. |
| 2019/0333210 A1* | 10/2019 | Mihalef ................ G06T 7/0012 |
| 2022/0084173 A1* | 3/2022 | Liang ..................... G06T 5/50 |

OTHER PUBLICATIONS

Comanichu, D; For Approximating Neural Network For Anatomical Object Detection Method And System; 2016 (Year: 2016).*
CN111182219—English Machine Translation; 31 pages.
EP patent application 22192785.8 filed Aug. 30, 2022—extended Search Report issued Oct. 17, 2022; 9 pages.
Tianling Lyu et al: "Dual-energy CT imaging from single-energy CT data with material decomposition convolutional neural network", Arxiv.Org, Cornell University Library, 201 Olin Library Cornell University Ithaca, NY 14853, May 30, 2020 (May 30, 2020), XP081685879.

* cited by examiner

LEARNING-BASED DOMAIN TRANSFORMATION FOR MEDICAL IMAGES

TECHNICAL FIELD

The subject disclosure relates generally to medical images, and more specifically to learning-based domain transformation for medical images.

BACKGROUND

A medical imaging device can capture a medical image of an anatomical structure of a patient for purposes of diagnosis and/or prognosis. There exist various medical scanning domains in which and/or by which the medical imaging device can capture the medical image. Different medical scanning domains can be implemented for different purposes and/or in different contexts. Although it may be desirable in some cases to capture the medical image in a particular medical scanning domain, it can sometimes be the case that the particular medical scanning domain is unavailable and that the medical image can be captured only in a different medical scanning domain. Unfortunately, there do not exist any systems and/or techniques that can address this problem.

Accordingly, systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate learning-based domain transformation for medical images are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a receiver component. In various cases, the receiver component can access a medical image. In various instances, the medical image can depict an anatomical structure according to a first medical scanning domain. In various aspects, the computer-executable components can further comprise a transformation component. In various cases, the transformation component can generate, via execution of a machine learning model, a predicted image based on the medical image. In various instances, the predicted image can depict the anatomical structure according to a second medical scanning domain that is different from the first medical scanning domain.

According to one or more embodiments, the above-described system can be implemented as a computer-implemented method and/or a computer program product.

DETAILED DESCRIPTION

Figure 1:
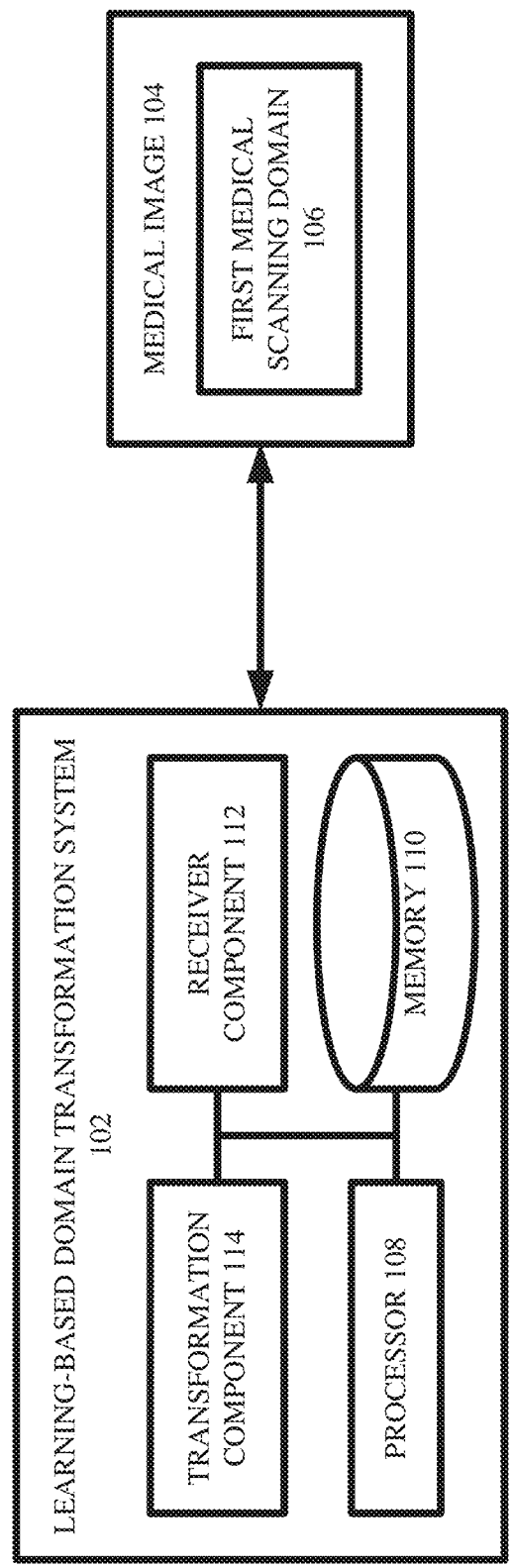
FIG. 1 illustrates a block diagram of an example, non-limiting system that facilitates learning-based domain transformation for medical images in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A medical imaging device (e.g., a computed tomography (CT) scanner, a magnetic resonance imaging (MRI) scanner, an X-ray scanner, an ultrasound scanner, a positron emission tomography (PET) scanner) can capture and/or generate a medical image (e.g., a CT image, an MRI image, an X-ray image, an ultrasound image, a PET image) of an anatomical structure of a patient for purposes of diagnosis and/or prognosis.

There exist various medical scanning domains in which and/or by which the medical imaging device can capture/generate the medical image. As those having ordinary skill in the art will appreciate, a medical scanning domain can be any suitable configurable setting, configurable control, and/or configurable parameter of the medical imaging device that can influence and/or otherwise affect how the medical image will visually appear once captured/generated. As a non-limiting example, a medical scanning domain can be a particular electrical energy level (e.g., measured in peak kilovoltage (kVp), measured in kilo electron volts (keV), and/or measured in milliamps (mA)) that is utilized by the medical imaging device to capture/generate the medical image. As those having ordinary skill in the art will appreciate, the medical image can exhibit various visual characteristics (e.g., a particular Hounsfield unit (HU) intensity distribution) if captured/generated via a low electrical energy level, and the medical image can exhibit different visual characteristics if captured/generated via a high electrical energy level. As another example, a medical scanning domain can be a particular contrast phase (e.g., non-contrast, early arterial phase, late arterial phase, hepatic phase, nephrogenic phase, venous phase, delayed phase) that is utilized by the medical imaging device to capture/generate the medical image. As above, the medical image can exhibit various visual characteristics if captured/generated using a given contrast phase, and the medical image can exhibit different visual characteristics if captured/generated using a different contrast phase.

Different medical scanning domains can be implemented for different purposes and/or in different contexts. For instance, there exist various computerized diagnostic techniques (e.g., tumor detection algorithms, calcium scoring algorithms, occlusion detection algorithms) that can automatically analyze the medical image so as to generate a diagnosis and/or prognosis for the patient. A particular computerized diagnostic technique can function by assuming that the medical image was captured/generated via a particular medical scanning domain. So, if the assumed medical scanning domain does not match the actual medical scanning domain that was used by the medical imaging device to capture/generate the medical image, the particular computerized diagnostic technique can yield inaccurate diagnosis/prognosis results.

Although it may be desirable in some cases to capture/generate the medical image via a certain medical scanning domain, it can sometimes be the case that the certain medical scanning domain is unavailable and that the medical image can be captured/generated only in a different medical scanning domain. For example, consider Agatston scoring, which is a particular automated technique for facilitating calcium scoring of CT images. In various aspects, it can be desired to apply Agatston scoring to a CT image of a patient, so that a calcium score can be generated for the patient. Note that Agatston scoring is defined for CT images that are captured/generated at 120 kVp. Thus, if the CT image of the patient is captured/generated at some energy level other than 120 kVp, Agatston scoring cannot be reliably applied to the CT image. However, 120 kVp can be considered as a rather high dose in current clinical practice, and capturing/generating the CT image at an energy level of 120 kVp can expose the patient to heightened levels of radiation which can increase the patient's risk of developing cancer. In this scenario, the patient's immediate health can be best served by capturing/generating a CT image at a lower energy level (e.g., 70 kVp), but such a CT image can exhibit increased levels of noise, lower visual quality, and/or other loss of detail and cannot then be accurately analyzed by Agatston scoring. This non-limiting example helps to illustrate how, in current clinical practice, some considerations (e.g., underlying assumptions of a computerized diagnostic technique that is desired to be applied to a medical image) might tend to favor utilizing one medical scanning domain (e.g., 120 kVp), while other countervailing considerations (e.g., desire to not expose patients to heightened radiation levels) might tend to favor utilizing a different medical scanning domain (e.g., 70 kVp).

Unfortunately, there do not exist any systems and/or techniques that can address this problem. To continue the above example, when existing techniques are implemented, either the CT image of the patient is captured/generated at 120 kVp, in which case the patient is exposed to dangerous levels of radiation, or the CT image of the patient is captured/generated at a lower energy level, in which case Agatston scoring cannot be accurately applied to the CT image. In other words, existing techniques cannot prevent the patient from being exposed to heightened radiation levels while also allowing the resulting CT image to be accurately analyzed by Agatston scoring.

Accordingly, systems and/or techniques that can address one or more of these technical problems can be desirable.

Various embodiments of the subject innovation can address one or more of these technical problems. One or more embodiments described herein include systems, computer-implemented methods, apparatus, and/or computer program products that can facilitate learning-based domain transformation for medical images. As mentioned above, it can often be the case that a particular medical scanning domain is preferred and/or desired to capture/generate a medical image, but despite such preference and/or desire, it can be the case that only a different medical scanning domain is available. As a solution to this technical problem, the inventors of various embodiments of the subject innovation devised learning-based domain transformation for medical images. In various aspects, learning-based domain transformation for medical images can involve training a machine learning model to receive as input a medical image that was captured/generated via a first medical scanning domain and to produce as output a version of the medical image according to a second medical scanning domain. In other words, the machine learning model can be configured to predict what the medical image would look like if it had been originally captured/generated via the second medical scanning domain. Accordingly, computerized diagnostic techniques that assume that the medical image was captured/generated via the second medical scanning domain can be applied to the predicted output yielded by the machine learning model, notwithstanding that the medical image was actually captured/generated via the first medical scanning domain.

In various instances, embodiments of the subject innovation can be considered as a computerized tool that can facilitate learning-based domain transformation for medical images. In various cases, the computerized tool described herein can comprise a receiver component and/or a transformation component.

In various embodiments, there can be a medical image that depicts an anatomical structure of a patient according to a first medical scanning domain. In various aspects, the anatomical structure can be any suitable body part and/or portion thereof of the patient, such as a brain, an eye, a lung, a heart, a kidney, an intestine, a vein, an artery, a bone, a chest, and/or an abdomen. In various instances, the medical image can be any suitable type of medical image, such as a CT image, an MRI image, an X-ray image, an ultrasound image, and/or a PET image. Moreover, in various cases, the medical image can have any suitable format and/or dimensionality. For ease of explanation, this disclosure will mainly describe the medical image as being a two-dimensional array of pixels. However, those having ordinary skill in the art will appreciate that various embodiments described herein are equally applicable when the medical image is a three-dimensional array of voxels (e.g., a cross-sectional slice of a three-dimensional array of voxels can itself be a two-dimensional array of pixels).

In various instances, the first medical scanning domain can be any suitable medical scanning domain as desired, such as a first electrical energy level and/or a first contrast phase. In various aspects, it can be desired to apply a computerized diagnostic technique to the medical image, where the computerized diagnostic technique assumes that the medical image was captured/generated via a second medical scanning domain that is different from the first medical scanning domain. For example, if the first medical scanning domain is a first electrical energy level, the second medical scanning domain can be a second electrical energy level that is different from the first electrical energy level. As another example, if the first medical scanning domain is a first contrast phase, the second medical scanning domain can be a second contrast phase that is different from the first contrast phase. In various instances, the computerized tool described herein can be configured to translate and/or transform the first medical scanning domain into the second medical scanning domain, such that the desired computerized diagnostic technique can be applied.

In various embodiments, the receiver component of the computerized tool can electronically receive and/or otherwise electronically access the medical image. In various aspects, the receiver component can retrieve the medical image from any suitable data structure (e.g., graph data structure, relational data structure, hybrid data structure) that is electronically accessible to the receiver component, whether the data structure is centralized and/or decentralized, and/or whether the data structure is remote from and/or local to the receiver component. For example, in some cases, the receiver component can retrieve the medical image from a medical imaging device (e.g., a CT scanner, an MRI scanner, an X-ray scanner, an ultrasound scanner, a PET scanner) that captured and/or generated the medical image. In any case, the receiver component can obtain and/or access the medical image, such that other components of the computerized tool can electronically interact with (e.g., read, write, manipulate) the medical image.

In various embodiments, the transformation component of the computerized tool can electronically generate, via execution and/or inferencing of a machine learning model, a predicted image based on the medical image. In various aspects, the machine learning model can be configured such that the predicted image depicts the anatomical structure according to the second medical scanning domain, instead of the first medical scanning domain. In other words, the medical image can be actually captured/generated via the first medical scanning domain, and the machine learning model can be configured to predict and/or infer what the medical image would look like if the medical image had been instead captured/generated according to the second medical scanning domain.

In various instances, the machine learning model can exhibit any suitable artificial intelligence architecture. As a non-limiting example, the machine learning model can exhibit a deep learning regression architecture. That is, the machine learning model can have any suitable number of neural network layers, can have any suitable numbers of neurons in various layers (e.g., different layers can have different numbers of neurons), can have any suitable types of activation functions in various neurons (e.g., softmax, sigmoid, hyperbolic tangent, rectified linear unit), and/or can have any suitable interneuron connectivity pattern (e.g., forward connections, skip connections, recursive connections, recurrent connections). In any case, the machine learning model can exhibit any suitable artificial intelligence architecture such that the machine learning model can receive as input the medical image, which is captured/generated in the first medical scanning domain, and can produce as output the predicted image, which represents how the medical image would look in the second medical scanning domain.

In various alternative embodiments, the computerized tool can further comprise a segmentation component. In various aspects, prior to executing the machine learning model on the medical image, the segmentation component can electronically identify, via execution and/or inferencing of a pre-trained segmentation model, a region-of-interest in the medical image. In various instances, the region-of-interest can be any suitable portion of the medical image (e.g., any suitable subset of pixels/voxels of the medical image) that is considered and/or deemed to be of interest from a diagnostic and/or prognostic perspective. For instance, the region-of-interest can be considered as a particular portion of the medical image on which it is desired to apply the computerized diagnostic technique. For example, in some cases, the region-of-interest can include the anatomical structure that is depicted in the medical image and can exclude background portions of the medical image. As another example, in some cases, the region-of-interest can include a specific portion of the anatomical structure and can exclude both a remaining portion of the anatomical structure and background portions of the medical image. In any case, once the segmentation component has identified the region-of-interest, the segmentation component can electronically crop out of the medical image any portions of the medical image that are not within the region-of-interest. As those having ordinary skill in the art will appreciate, the pre-trained segmentation model can exhibit any suitable architecture as desired (e.g., can be a deep learning segmentation model) and can be trained via any suitable learning paradigm (e.g., supervised training, unsupervised training, reinforcement learning).

Although the segmentation component can be configured to identify the region-of-interest and to crop out portions of the medical image that are not within the region-of-interest, those having ordinary skill in the art will appreciate that this is a mere non-limiting example. In various cases, the segmentation component can instead be configured to identify one or more regions-of-disinterest in the medical image and to crop out such one or more regions-of-disinterest. In any case, the segmentation component can produce a cropped version of the medical image that includes one or more regions-of-interest and that excludes one or more regions-of-disinterest and/or one or more background regions.

In various aspects, after the segmentation component has cropped out of the medical image any portions that are not within the region-of-interest, the transformation component can execute the machine learning model on the cropped medical image, thereby causing the machine learning model to output a cropped predicted image. Because the cropped medical image can depict only the region-of-interest according to the first medical scanning domain, the cropped predicted image can correspondingly depict only the region-of-interest according to the second medical scanning domain. In various aspects, by configuring the machine learning model to receive as input the cropped medical image (e.g., which contains fewer pixels/voxels than the full medical image) and to produce as output the cropped predicted image (e.g., which contains fewer pixels/voxels than the full predicted image), the machine learning model can be considered as focusing on transforming the domain of the region-of-interest without getting bogged down and/or distracted by transforming the domain of the background portions of the medical image. In various cases, this can allow the machine learning model to achieve a higher level of performance accuracy than would otherwise be possible.

In various alternative embodiments, the computerized tool can further comprise a denoise component. In various aspects, prior to the execution of the pre-trained segmentation model on the medical image, the denoise component can electronically evaluate a noise level of the medical image. If the denoise component determines that the noise level does not exceed any suitable threshold value, the denoise component can refrain from taking further action. On the other hand, if the denoise component determines that the noise level exceeds any suitable threshold value, the denoise component can electronically apply one or more denoising techniques to the medical image. In various instances, any suitable denoising techniques can be implemented. For example, in some cases, the denoise component can apply a denoise filter to the medical image, thereby reducing the noise level of the medical image. In other cases, the denoise component can execute a pre-trained denoising model on the medical image, which can be configured to output a denoised version of the medical image. As those having ordinary skill in the art will appreciate, the pre-trained denoise model can exhibit any suitable artificial intelligence architecture as desired (e.g., can be a deep learning model) and can be trained via any suitable learning paradigm (e.g., supervised training, unsupervised training, reinforcement learning).

In various aspects, after the denoise component has applied one or more denoise techniques to the medical image, the segmentation component can crop out background portions of the denoised medical image, and the transformation component can execute the machine learning model on the denoised and cropped medical image, thereby yielding a denoised and cropped predicted image. Those having ordinary skill in the art will appreciate that, in some cases, the order of application of denoising and segmentation can be switched as desired. That is, in various aspects, the segmentation component can be configured to crop out of the medical image any background portions, the denoise component can be configured to apply one or more denoising techniques to the cropped medical image, and the transformation component can be configured to execute the machine learning model on the cropped and denoised medical image. In any case, the performance of the machine learning model can be further improved when the denoise component is implemented (e.g., the machine learning model can be not distracted by excessive noise in the medical image).

In various embodiments, the computerized tool can further comprise an execution component. In various aspects, after the transformation component has executed the machine learning model on the medical image (e.g., which can be cropped and/or denoised, as mentioned above) so as to yield the predicted image, the execution component can electronically apply the computerized diagnostic technique to the predicted image. Accordingly, the execution component can yield one or more diagnostic and/or prognostic results for the patient, and the execution component can electronically transmit such results to any suitable computing device as desired.

In order for the machine learning model to facilitate accurate transformation of the first medical scanning domain to the second medical scanning domain, the machine learning model first requires training. Accordingly, in various embodiments, the computerized tool can further comprise a training component. In various aspects, prior to execution and/or inferencing of the machine learning model, the receiver component can electronically access a training dataset, and the training component can electronically train the machine learning model on the training dataset.

More specifically, the training dataset can include a set of training images and a set of annotation images that respectively correspond to the set of training images. That is, each training image in the set of training images can respectively correspond to a unique annotation image in the set of annotation images. Consider a particular training image that corresponds to a particular annotation image. In various aspects, the particular training image can depict one or more anatomical structures according to the first medical scanning domain. In contrast, the particular annotation image can depict the same one or more anatomical structures according to the second medical scanning domain. Moreover, in various instances, the particular training image can be registered and/or aligned with the particular annotation image. In various aspects, such registration and/or alignment can be facilitated in any suitable fashion. For example, in some cases, the particular training image can be co-registered with the particular annotation image through simulation, through scanning physical phantoms, and/or through dual-energy scans. As another example, in some cases, the particular annotation image can be fixed and the particular training image can be iteratively perturbed (e.g., iteratively rotated counter-clockwise and/or clockwise, iteratively shifted up and/or down, iteratively shifted left and/or right) until pixel-to-pixel (or voxel-to-voxel) registration is achieved between the particular training image and the particular annotation image. As yet another example, in other cases, the particular training image can be fixed and the particular annotation image can be iteratively perturbed (e.g., iteratively rotated counter-clockwise and/or clockwise, iteratively shifted up and/or down, iteratively shifted left and/or right) until pixel-to-pixel (or voxel-to-voxel) registration is achieved between the particular training image and the particular annotation image. As yet another example, in some cases, a pre-trained registration model (e.g., deep learning model) can be executed on the particular training image and/or the particular annotation image, so as to ensure registration/alignment. In any case, the particular training image and the particular annotation image can be registered and/or aligned, such that the one or more anatomical structures depicted in the particular training image have the same respective coordinates as the one or more anatomical structures depicted in the particular annotation image.

In embodiments where the segmentation component and denoise component are not implemented, the training component can train the machine learning model on the training dataset as follows. In various instances, the internal parameters (e.g., weights, biases) of the machine learning model can be randomly initialized. In various cases, the training component can select a training image from the training dataset. In various aspects, the training component can register/align the selected training image with its corresponding annotation image, if such registration/alignment has not already been facilitated. In various instances, the training component can feed the selected training image as input to the machine learning model. This can cause the machine learning model to generate as output a predicted image, where the predicted image represents how the selected training image would look if the selected training image were captured/generated via the second medical scanning domain rather than the first medical scanning domain. If the machine learning model has so far undergone no and/or little training, the predicted image can be rather inaccurate. In various instances, the training component can compute an error/loss between the predicted image and the corresponding annotation image. Accordingly, the training component can update, via backpropagation, the internal parameters of the machine learning model based on the computed error/loss.

In various cases, the training component can repeat this procedure for each training image in the training dataset, thereby causing the internal parameters of the machine learning model to become iteratively optimized for transforming the first medical scanning domain to the second medical scanning domain. As those having ordinary skill in the art will appreciate, any suitable training batch sizes and/or training epochs can be implemented.

In embodiments where the segmentation component is implemented and where the denoise component is not implemented, the training component can train the machine learning model on the training dataset as follows. In various instances, the internal parameters (e.g., weights, biases) of the machine learning model can be randomly initialized. In various cases, the training component can select a training image from the training dataset. In various aspects, the training component can register/align the selected training image with its corresponding annotation image, if such registration/alignment has not already been facilitated. In various instances, the segmentation component can identify, via execution of the segmentation model, a region-of-interest in the selected training image and can identify the same region-of-interest in the corresponding annotation image. Accordingly, the segmentation component can crop out of the selected training image any portions of the selected training image that are not within the region-of-interest. Similarly, the segmentation component can crop out of the corresponding annotation image any portions of the corresponding annotation image that are not within the region-of-interest. In various aspects, the training component can feed the cropped selected training image as input to the machine learning model. This can cause the machine learning model to generate as output a cropped predicted image, where the cropped predicted image represents how the cropped selected training image would look if the cropped selected training image were captured/generated via the second medical scanning domain rather than the first medical scanning domain. If the machine learning model has so far undergone no and/or little training, the cropped predicted image can be rather inaccurate. In various instances, the training component can compute an error/loss between the cropped predicted image and the cropped corresponding annotation image. Accordingly, the training component can update, via backpropagation, the internal parameters of the machine learning model based on the computed error/loss.

As mentioned above, the training component can repeat this procedure for each training image in the training dataset, thereby causing the internal parameters of the machine learning model to become iteratively optimized for transforming the first medical scanning domain to the second medical scanning domain. As also mentioned above, when the machine learning model is trained based on cropped versions of the training images and cropped versions of the annotation images, the machine learning model can be considered as being able to focus on the region-of-interest, without getting distracted by background portions. Such focusing can cause the machine learning model to be trained more quickly and/or to achieve a higher degree of performance accuracy. Again, any suitable training batch sizes and/or training epochs can be implemented.

In embodiments where the segmentation component and the denoise component are both implemented, the training component can train the machine learning model on the training dataset as follows. In various instances, the internal parameters (e.g., weights, biases) of the machine learning model can be randomly initialized. In various cases, the training component can select a training image from the training dataset. In various aspects, the training component can register/align the selected training image with its corresponding annotation image, if such registration/alignment has not already been facilitated. In various instances, the denoise component can evaluate the noise level of the selected training image and of the corresponding annotation image. Based on such evaluation, the denoise component can apply one or more denoising techniques to both the selected training image and the corresponding annotation image, as appropriate. In various cases, the segmentation component can identify, via execution of the segmentation model, a region-of-interest in the denoised selected training image and can identify the same region-of-interest in the denoised corresponding annotation image. Accordingly, the segmentation component can crop out of the denoised selected training image any portions of the denoised selected training image that are not within the region-of-interest. Similarly, the segmentation component can crop out of the denoised corresponding annotation image any portions of the denoised corresponding annotation image that are not within the region-of-interest. In various aspects, the training component can feed the denoised and cropped selected training image as input to the machine learning model. This can cause the machine learning model to generate as output a denoised and cropped predicted image, where the denoised and cropped predicted image represents how the denoised and cropped selected training image would look if the denoised and cropped selected training image were captured/generated via the second medical scanning domain rather than the first medical scanning domain. If the machine learning model has so far undergone no and/or little training, the denoised and cropped predicted image can be rather inaccurate. In various instances, the training component can compute an error/loss between the denoised and cropped predicted image and the denoised and cropped corresponding annotation image. Accordingly, the training component can update, via backpropagation, the internal parameters of the machine learning model based on the computed error/loss.

As mentioned above, the training component can repeat this procedure for each training image in the training dataset, thereby causing the internal parameters of the machine learning model to become iteratively optimized for transforming the first medical scanning domain to the second medical scanning domain. As also mentioned above, when the machine learning model is trained based on denoised and cropped versions of the training images and denoised and cropped versions of the annotation images, the machine learning model can be considered as being able to focus on the region-of-interest, without getting distracted by background portions and/or by noise. Again, any suitable training batch sizes and/or training epochs can be implemented.

Those having ordinary skill in the art will appreciate that, when the denoise component is implemented with the segmentation component, the denoise component can apply the one or more denoising techniques to the selected training image and/or to the corresponding annotation image before the segmentation component crops such images (as described above) and/or after the segmentation component crops such images. That is, the order of application of denoising and segmentation can be switched in any suitable fashion as desired.

Moreover, those having ordinary skill in the art will appreciate that the training component can, in various embodiments, implement any suitable loss, error, and/or objective functions to facilitate training of the machine learning model. In some cases, the loss, error, and/or objective function can be customized and/or otherwise based on operational context of the machine learning model. For instance, any suitable constraints can be added to and/or otherwise incorporated into the loss, error, and/or objective function, based on the specific computerized diagnostic technique that is desired to be applied to the output of the machine learning model. As a non-limiting example, suppose that it is desired to apply Agatston scoring to the predicted image that is outputted by the machine learning model during inferencing. In such cases, because Agatston scoring is a type of calcium scoring technique, it can be desired that the machine learning model be highly accurate when shifting the medical scanning domain of depicted calcification regions. Thus, higher weights can be assigned to such calcification regions in the loss, error, and/or objective function, and lower weights can be assigned to non-calcification regions, so that the training of the machine learning model is biased toward getting higher accuracy on the calcification regions. Moreover, since Agatston scoring works by classifying different pixels/voxels into four different calcification categories, it can be desired to ensure that the machine learning model transforms intensities of pixels/voxels to be in accordance with the target medical scanning domain without changing the Agatston categories of such pixels/voxels. Accordingly, the loss, error, and/or objective function can include a penalty that is applied whenever the machine learning model causes an Agatston category change during training, so as to bias the machine learning model against causing such category changes. Those having ordinary skill in the art will appreciate that these are mere non-limiting examples of ways in which the loss, error, and/or objective function can be customized and/or manipulated, based on the desired diagnostic technique to be applied to the inferencing output of the machine learning model.

In various aspects, the computerized tool described herein can electronically receive a medical image that has been captured/generated via an input medical scanning domain and can electronically execute a machine learning model on the medical image, wherein the machine learning model is configured to translate and/or transform the input medical scanning domain into a target medical scanning domain. Thus, diagnostic techniques that can only be applied to medical images that are captured/generated via the target medical scanning domain can nevertheless be implemented.

Various embodiments of the subject innovation can be employed to use hardware and/or software to solve problems that are highly technical in nature (e.g., to facilitate learning-based domain transformation for medical images), that are not abstract and that cannot be performed as a set of mental acts by a human. Further, some of the processes performed can be performed by a specialized computer (e.g., domain transformation machine learning model, pre-trained segmentation model, pre-trained registration model) for carrying out defined tasks related to learning-based domain transformation for medical images. For example, such defined tasks can include: accessing, by a device operatively coupled to a processor, a medical image, wherein the medical image depicts an anatomical structure according to a first medical scanning domain; and generating, by the device and via execution of a machine learning model, a predicted image based on the medical image, wherein the predicted image depicts the anatomical structure according to a second medical scanning domain that is different from the first medical scanning domain. Such defined tasks are not performed manually by humans. Indeed, neither the human mind nor a human with pen and paper can electronically receive a medical image that has been captured/generated via a given medical scanning domain and can electronically execute a machine learning model on the medical image to generate a predicted image, where the predicted image can be considered as representing how the medical image would have looked if it had been captured/generated via a different medical scanning domain. Instead, various embodiments of the subject innovation are inherently and inextricably tied to computer technology and cannot be implemented outside of a computing environment (e.g., machine learning models are concrete and tangible combinations of computer-executable hardware and/or computer-executable software; thus, a computerized tool that executes a domain transformation machine learning model on a medical image so as to shift and/or transform the medical scanning domain of the medical image is itself an inherently-computerized device that cannot be practicably implemented in any sensible way without computers).

Moreover, various embodiments of the subject innovation can integrate into a practical application various teachings described herein relating to the field of medical imaging. As explained above, there exist various different medical scanning domains (e.g., high electrical energy vs. low electrical energy, arterial contrast phase vs. delayed contrast phase) that can be implemented in various different contexts. Specifically, it is often the case that a diagnostic technique is desired to be applied to a medical image and that such diagnostic technique assumes that the medical image was captured/generated via a certain medical scanning domain. However, there may be any number of reasons why the certain medical scanning domain is unavailable (e.g., using high electrical energy and/or high radiation can be dangerous to the health of the patient). In such case, the medical image would have to be captured/generated via some other medical scanning domain. When the other medical scanning domain is used, existing techniques offer no solution for accurately and/or reliably applying the desired diagnostic technique to the medical image. In stark contrast, various embodiments of the subject innovation can solve this problem. Specifically, the computerized tool described herein can execute a machine learning model on the medical image, and the output of such machine learning model can be and/or represent how the medical image would have looked if it had been captured/generated by the certain medical scanning domain rather than the other medical scanning domain. So, the desired diagnostic technique can be accurately and/or reliably applied to the predicted image. In other words, the computerized tool described herein can transform an inputted medical image from one medical scanning domain to another medical scanning domain, so that diagnostic techniques that can only be used in conjunction with the another medical scanning domain can be applied to the medical image. Accordingly, the computerized tool described herein can be considered as a concrete and tangible technical improvement in the field of medical imaging, and thus clearly constitutes a useful and practical application of computers.

Furthermore, various embodiments of the subject innovation can control real-world tangible devices based on the disclosed teachings. For example, various embodiments of the subject innovation can electronically execute a real-world domain transformation machine learning model on a real-world medical image, so as to generate a real-world predicted image that represents how the real-world medical image would have looked in a different medical scanning domain. Moreover, the computerized tool can, in some cases, actually execute one or more real-world diagnostic techniques (e.g., Agatston scoring) on the real-world predicted image, so as to yield real-world diagnosis/prognosis results for a real-world medical patient.

It should be appreciated that the herein figures and description provide non-limiting examples of the subject innovation and are not necessarily drawn to scale.

FIG. 1 illustrates a block diagram of an example, non-limiting system 100 that can facilitate learning-based domain transformation for medical images in accordance with one or more embodiments described herein. As shown, a learning-based domain transformation system 102 can be electronically integrated, via any suitable wired and/or wireless electronic connection, with a medical image 104.

In various embodiments, the medical image 104 can depict an anatomical structure of a patient (e.g., human, animal, and/or otherwise). In various aspects, the anatomical structure can be any suitable body part, and/or portion thereof, of the patient. For example, the anatomical structure can be a head, a neck, a chest, an abdomen, an arm, a leg, a hand, a foot, a brain, an eye, an ear canal, a tongue, an esophagus, a trachea, a heart, a lung, a stomach, an intestine, a vein, an artery, a bone, and/or any other suitable body part and/or portion thereof. In various instances, the medical image 104 can be any suitable type of medical image that is captured/generated by any suitable medical scanning modality. As a non-limiting example, the medical image 104 can be a CT image that is captured/generated by a CT scanner. As another example, the medical image 104 can be an MRI image that is captured/generated by an MRI scanner. As yet another example, the medical image 104 can be an X-ray image that is captured/generated by an X-ray scanner. As still another example, the medical image 104 can be an ultrasound image that is captured/generated by an ultrasound scanner. As even another example, the medical image 104 can be a PET image that is captured/generated by a PET scanner.

In various cases, the medical image 104 can have any suitable dimensionality. For example, in some cases, the medical image 104 can be a two-dimensional array of pixels, where each pixel exhibits a Hounsfield unit (HU) intensity value. As another example, in other cases, the medical image 104 can be a three-dimensional array of voxels, where each voxel exhibits an HU intensity value. For ease of explanation, the herein disclosure mainly describes the medical image 104 as a two-dimensional array of pixels. However, those having ordinary skill in the art will appreciate that the herein teachings are equally applicable to three-dimensional arrays of voxels. Indeed, a two-dimensional slice (e.g., axial slice, coronal slice, sagittal slice) of a three-dimensional array of voxels can itself be considered as a two-dimensional array of pixels.

In various aspects, the medical image 104 can depict the anatomical structure according to a first medical scanning domain 106. In various instances, the first medical scanning domain 106 can be any suitable configurable setting, configurable control, and/or configurable parameter of the medical scanning modality that captured/generated the medical image 104, where such configurable setting, configurable control, and/or configurable parameter can influence and/or otherwise affect how the medical image 104 visually appears once captured/generated. As a non-limiting example, the first medical scanning domain 106 can be an electrical energy level with which the medical scanning modality captures/generates the medical image 104. After all, capturing/generating the medical image 104 via a low electrical energy level (e.g., 70 kVp) can cause the medical image 104 to depict the anatomical structure using a given HU intensity distribution, whereas capturing/generating the medical image 104 via a high electrical energy level (e.g., 120 kVp) can cause the medical image 104 to depict the anatomical structure using a different HU intensity distribution. As another non-limiting example, the first medical scanning domain 106 can be a contrast phase with which the medical scanning modality captures/generates the medical image 104. After all, capturing/generating the medical image 104 via a first contrast phase (e.g., one of non-contrast, early arterial phase, late arterial phase, hepatic phase, nephrogenic phase, venous phase, and/or delayed phase) can cause the medical image 104 to depict the anatomical structure using a given HU intensity distribution, whereas capturing/generating the medical image 104 via a different contrast phase (e.g., a different one of non-contrast, early arterial phase, late arterial phase, hepatic phase, nephrogenic phase, venous phase, and/or delayed phase) can cause the medical image 104 to depict the anatomical structure using a different HU intensity distribution. Those having ordinary skill in the art will understand that, in some cases, the first medical scanning domain 106 can be both an electrical energy level and a contrast phase (e.g., a single CT image can be captured/generated at both a given electrical energy level and a given contrast phase). In such cases, the first medical scanning domain 106 can be considered and/or referred to as an energy-contrast pair.

Accordingly, in various aspects, the first medical scanning domain 106 can be a first electrical energy level and/or a first contrast phase that is utilized by the medical scanning modality to capture/generate the medical image 104.

In various cases, it can be desired to apply a computerized diagnostic technique to the medical image 104. In various cases, the computerized diagnostic technique can be any suitable model and/or algorithm that is configured to identify one or more pathologies in the medical image 104. As a non-limiting example, the computerized diagnostic technique can be a tumor detection algorithm. As another example, the computerized diagnostic technique can be an occlusion detection algorithm. As still another example, the computerized diagnostic technique can be a calcification scoring algorithm, such as Agatston scoring. In any case, the computerized diagnostic technique can assume and/or otherwise rely on the assumption that the medical image 104 is captured/generated by a second medical scanning domain that is different from the first medical scanning domain 106. For example, if the first medical scanning domain 106 is a first electrical energy level, then the second medical scanning domain can be a different electrical energy level. As another example, if the first medical scanning domain 106 is a first contrast phase, then the second medical scanning domain can be a different contrast phase. As still another example, if the first medical scanning domain 106 is a first energy-contrast pair, then the second medical scanning domain can be a different energy-contrast pair. Because the first medical scanning domain 106 does not match the medical scanning domain that is assumed by the computerized diagnostic technique, the computerized diagnostic technique can be unable to be reliably and/or accurately applied to the medical image 104. In various cases, the learning-based domain transformation system 102 can solve this problem.

In various embodiments, the learning-based domain transformation system 102 can comprise a processor 108 (e.g., computer processing unit, microprocessor) and a computer-readable memory 110 that is operably and/or operatively and/or communicatively connected/coupled to the processor 108. The computer-readable memory 110 can store computer-executable instructions which, upon execution by the processor 108, can cause the processor 108 and/or other components of the learning-based domain transformation system 102 (e.g., receiver component 112, transformation component 114) to perform one or more acts. In various embodiments, the computer-readable memory 110 can store computer-executable components (e.g., receiver component 112, transformation component 114), and the processor 108 can execute the computer-executable components.

In various embodiments, the learning-based domain transformation system 102 can comprise a receiver component 112. In various aspects, the receiver component 112 can electronically receive and/or otherwise electronically access the medical image 104. In various instances, the receiver component 112 can electronically retrieve the medical image 104 from any suitable data structure, database, and/or computing device (not shown) that is electronically accessible to the receiver component 112. For example, the receiver component 112 can electronically retrieve the medical image 104 from the medical scanning modality (e.g., CT scanner, MRI scanner, X-ray scanner, ultrasound scanner, PET scanner) that captured/generated the medical image 104. In any case, the receiver component 112 can electronically obtain and/or access the medical image 104, such that other components of the learning-based domain transformation system 102 can electronically interact with the medical image 104.

In various embodiments, the learning-based domain transformation system 102 can comprise a transformation component 114. In various aspects, the transformation component 114 can electronically store, maintain, control, and/or otherwise access a machine learning model. In various instances, the machine learning model can be configured to transform, translate, shift, and/or otherwise convert the first medical scanning domain 106 of the medical image 104 into the second medical scanning domain. More specifically, the machine learning model can be configured to receive as input the medical image 104 and to produce as output a predicted image, where the predicted image depicts the same anatomical structure as the medical image 104, but where the predicted image exhibits an HU intensity distribution according to the second medical scanning domain, rather than according to the first medical scanning domain 106. In other words, the predicted image can be considered as representing how the medical image 104 would look if it had been captured/generated according to the second medical scanning domain instead of the first medical scanning domain 106. Accordingly, the computerized diagnostic technique, which can only be accurately applied to medical images that are captured/generated via the second medical scanning domain, can be accurately applied to the predicted image. In this way, the medically-relevant information that is represented by the medical image 104 can be analyzed by the computerized diagnostic technique, notwithstanding that the medical image 104 is captured/generated via a medical scanning domain that is not consistent with the underlying assumptions of the computerized diagnostic technique. This certainly constitutes a concrete and tangible technical improvement.

Although not shown in FIG. 1, the learning-based domain transformation system 102 can, in various embodiments, comprise an execution component. In various aspects, the execution component can electronically apply the computerized diagnostic technique to the predicted image that is outputted by the machine learning model of the transformation component 114, thereby yielding one or more diagnostic/prognostic results. In various instances, the execution component can electronically transmit such diagnostic/prognostic results to any suitable computing device.

Although not explicitly shown in FIG. 1, the learning-based domain transformation system 102 can comprise a segmentation component. In various aspects, the segmentation component can electronically store, maintain, control, and/or otherwise access a pre-trained segmentation model. In various instances, the pre-trained segmentation model can be configured to receive as input the medical image 104 and to identify as output a region-of-interest that is depicted within the medical image 104. In some cases, the region-of-interest can be the anatomical structure. In other cases, the region-of-interest can be a specific sub-portion of the anatomical structure. In any case, the pre-trained segmentation model can be configured to identify and/or mask the region-of-interest, and the segmentation component can electronically crop out of the medical image 104 any pixels/voxels that do not make up the region-of-interest. In this way, background portions of the medical image 104 can be eliminated and/or deleted, so that only the region-of-interest remains in the medical image 104. In such embodiments, the machine learning model can be configured to receive as input the cropped version of the medical image 104, and the predicted image that is outputted by the machine learning model can have the same dimensions (e.g., same number and/or arrangement of pixels/voxels) as the cropped version of the medical image 104. In various cases, by configuring the machine learning model to operate on the cropped version of the medical image 104, the machine learning model can be considered as focusing on shifting the medical scanning domain of the region-of-interest, without getting distracted by unimportant background portions of the medical image 104. In other words, the machine learning model can, in some cases, achieve higher performance accuracy when configured to receive as input the cropped version of the medical image 104.

Although not explicitly shown in FIG. 1, the learning-based domain transformation system 102 can further comprise a denoise component. In various aspects, the denoise component can electronically evaluate and/or measure a visual noise level that is exhibited by the medical image 104. If the visual noise level does not exceed any suitable threshold value, the denoise component can refrain from taking further action. In such case, the segmentation component can crop the medical image 104 so that it depicts only the region-of-interest, and the transformation component 114 can execute the machine learning model on the cropped version of the medical image 104. On the other hand, if the visual noise level exceeds any suitable threshold value, the denoise component can electronically apply any suitable denoising technique (e.g., denoising filter, deep learning denoising model) to the medical image 104, so as to reduce and/or eliminate the visual noise of the medical image 104. After such denoising, the segmentation component can crop the denoised version of the medical image 104 so that it depicts only the region-of-interest, and the transformation component 114 can execute the machine learning model on the cropped and denoised version of the medical image 104. As those having ordinary skill in the art will appreciate, application of denoising to the medical image 104 can allow the machine learning model to achieve a higher degree of performance accuracy. As those having ordinary skill in the art will further appreciate, in some cases, the denoise component can apply the denoising technique to the medical image 104 prior to cropping by the segmentation component, and in other cases, the segmentation component can crop the medical image 104 prior to application of the denoising technique by the denoise component.

Although not explicitly shown in FIG. 1, the learning-based domain transformation system 102 can comprise a training component. In various aspects, the receiver component 112 can electronically receive and/or access a training dataset, and the training component can electronically train the machine learning model on the training dataset to accurately shift, covert, and/or transform the first medical scanning domain 106 to the second medical scanning domain. More specifically, the training dataset can include a set of training images, each of which is captured/generated via the first medical scanning domain 106, and a respectively corresponding set of annotation images, each of which is captured/generated via the second medical scanning domain. Consider a given training image in the set of training images, where the given training image depicts one or more anatomical structures according to the first medical scanning domain 106. In such case, there can be a given annotation image in the set of annotation images that corresponds to the given training image, where the given annotation image depicts the same one or more anatomical structures as the given training image, but where the given annotation image depicts such one or more anatomical structures according to the second medical scanning domain instead of the first medical scanning domain 106. In other words, the given annotation image can be considered as representing how the given training image would actually look if the given training image had been captured/generated via the second medical scanning domain. In various aspects, the training component can input the given training image (with or without cropping by the segmentation component and/or denoising by the denoise component, as desired) to the machine learning model. This can cause the machine learning model to generate a predicted output image, where the predicted output image represents the machine learning model's estimation of how the given training image would look if captured/generated according to the second medical scanning domain. In various instances, the training component can compute an error/loss between the predicted output image and the given annotation image, and the training component can update (e.g., via backpropagation) internal parameters of the machine learning model based on such error/loss. In various cases, the training component can repeat this for each training image in the set of training images, with the ultimate result being that the internal parameters of the machine learning model become optimized. In other words, such training can cause the machine learning model to learn how to accurately transform and/or convert the first medical scanning domain 106 to the second medical scanning domain. Those having ordinary skill in the art will appreciate that any suitable batch sizes, any suitable number of epochs, and/or any suitable style of error/loss function can be implemented as desired.

Figure 2:
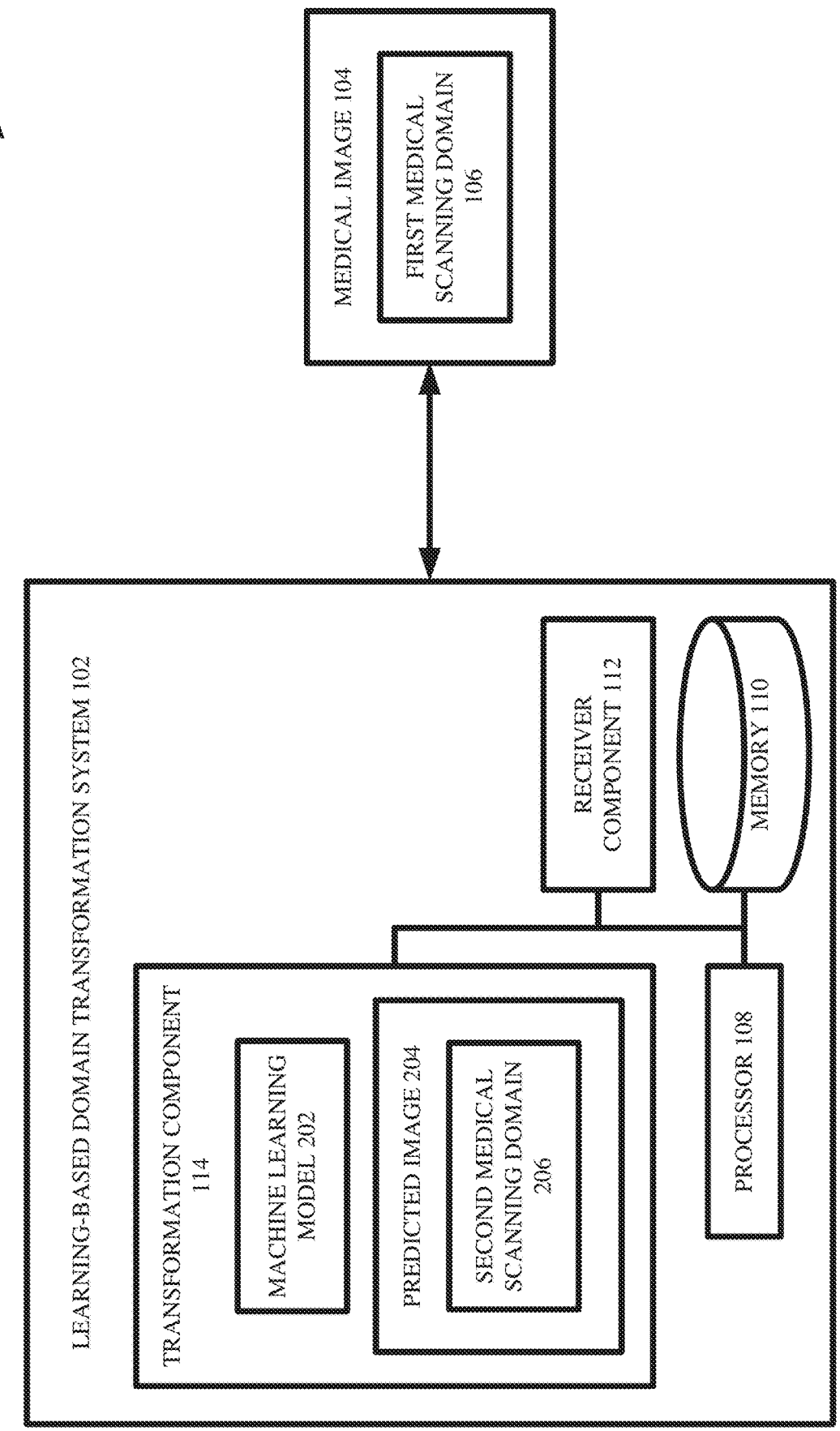
FIG. 2 illustrates a block diagram of an example, non-limiting system including a machine learning model that facilitates learning-based domain transformation for medical images in accordance with one or more embodiments described herein.

FIG. 2 illustrates a block diagram of an example, non-limiting system 200 including a machine learning model that can facilitate learning-based domain transformation for medical images in accordance with one or more embodiments described herein. As shown, the system 200 can, in some cases, comprise the same components as the system 100, and can further comprise a machine learning model 202 and/or a predicted image 204.

In various embodiments, the transformation component 114 can electronically store, electronically maintain, electronically operate, and/or otherwise electronically access the machine learning model 202. In various aspects, the machine learning model 202 can exhibit any suitable artificial intelligence architecture. As a non-limiting example, the machine learning model 202 can be a deep learning regression model that comprises any suitable number of neural network layers, that comprises any suitable numbers of neurons in various layers (e.g., different layers can have different numbers of neurons), that comprises any suitable activation functions (e.g., softmax, sigmoid, hyperbolic tangent, rectified linear unit) in various neurons (e.g., different neurons can have different activation functions), and/or that comprises any suitable interneuron connectivity pattern (e.g., forward connections, skip connections, recursive connections). In any case, the transformation component 114 can electronically execute the machine learning model 202 on the medical image 104, thereby yielding the predicted image 204. In other words, the machine learning model 202 can be configured to receive as input the medical image 104 and to produce as output the predicted image 204. For example, if the machine learning model 202 is a deep learning regression model, the medical image 104 can complete a forward pass through an input layer, one or more hidden layers, and an output layer of the machine learning model 202, with the result generated by the output layer being the predicted image 204.

As mentioned above, the medical image 104 can depict an anatomical structure of a patient according to the first medical scanning domain 106. In various aspects, the predicted image 204 can depict the same anatomical structure of the patient, but the predicted image 204 can do so according to a second medical scanning domain 206, where the second medical scanning domain 206 is different from the first medical scanning domain 106. As an example, if the first medical scanning domain 106 is a particular electrical energy level (e.g., 70 kVp), the second medical scanning domain 206 can be a different electrical energy level (e.g., 120 kVp). As another example, if the first medical scanning domain 106 is a particular contrast phase (e.g., one of non-contrast, early arterial phase, late arterial phase, hepatic phase, nephrogenic phase, venous phase, and/or delayed phase), the second medical scanning domain 206 can be a different contrast phase (e.g., a different one of non-contrast, early arterial phase, late arterial phase, hepatic phase, nephrogenic phase, venous phase, and/or delayed phase). As yet another example, if the first medical scanning domain 106 is a particular energy-contrast pair (e.g., a CT image captured/generated at 70 kVp during the late arterial contrast phase), the second medical scanning domain 206 can be a different energy-contrast pair (e.g., appearing to be a CT image captured/generated at 120 kVp during a non-contrast phase).

In other words, the medical image 104 can exhibit an HU intensity distribution that visually resembles the anatomical structure of the patient and that is consistent with and/or otherwise determined by the first medical scanning domain 106, while the predicted image 204 can exhibit an HU intensity distribution that visually resembles the same anatomical structure of the same patient but that is instead consistent with and/or otherwise determined by the second medical scanning domain 206. In still other words, the predicted image 204 can be considered as showing and/or otherwise representing how the medical image 104 would have visually appeared and/or looked if the medical image 104 had been captured/generated via the second medical scanning domain 206 rather than the first medical scanning domain 106.

Those having ordinary skill in the art will appreciate that the predicted image 204 can, in various aspects, have the same format as the medical image 104. For example, if the medical image 104 is a CT image captured/generated via the first medical scanning domain 106, then the predicted image 204 can likewise appear to be a CT image, but one that is captured/generated via the second medical scanning domain 206 instead of the first medical scanning domain 106. As another example, if the medical image 104 is an X-ray image captured/generated via the first medical scanning domain 106, then the predicted image 204 can likewise appear to be an X-ray image, but one that is captured/generated via the second medical scanning domain 206 rather than the first medical scanning domain 106. As yet another example, if the medical image 104 is an MRI image captured/generated via the first medical scanning domain 106, then the predicted image 204 can likewise appear to be an MRI image, but one that is captured/generated via the second medical scanning domain 206 instead of the first medical scanning domain 106. As still another example, if the medical image 104 is an ultrasound image captured/generated via the first medical scanning domain 106, then the predicted image 204 can likewise appear to be an ultrasound image, but one that is captured/generated via the second medical scanning domain 206 rather than the first medical scanning domain 106. As even another example, if the medical image 104 is a PET image captured/generated via the first medical scanning domain 106, then the predicted image 204 can likewise appear to be a PET image, but one that is captured/generated via the second medical scanning domain 206 instead of the first medical scanning domain 106.

Those having ordinary skill in the art will further appreciate that the predicted image 204 can, in various aspects, have the same dimensionality as the medical image 104. For example, if the medical image 104 is a two-dimensional array of pixels, then the predicted image 204 can likewise be a two-dimensional array of pixels (e.g., the predicted image 204 can have the same number and/or arrangement of pixels as the medical image 104). As another example, if the medical image 104 is a three-dimensional array of voxels, then the predicted image 204 can likewise be a three-dimensional array of voxels (e.g., the predicted image 204 can have the same number and/or arrangement of voxels as the medical image 104).

Figure 3:
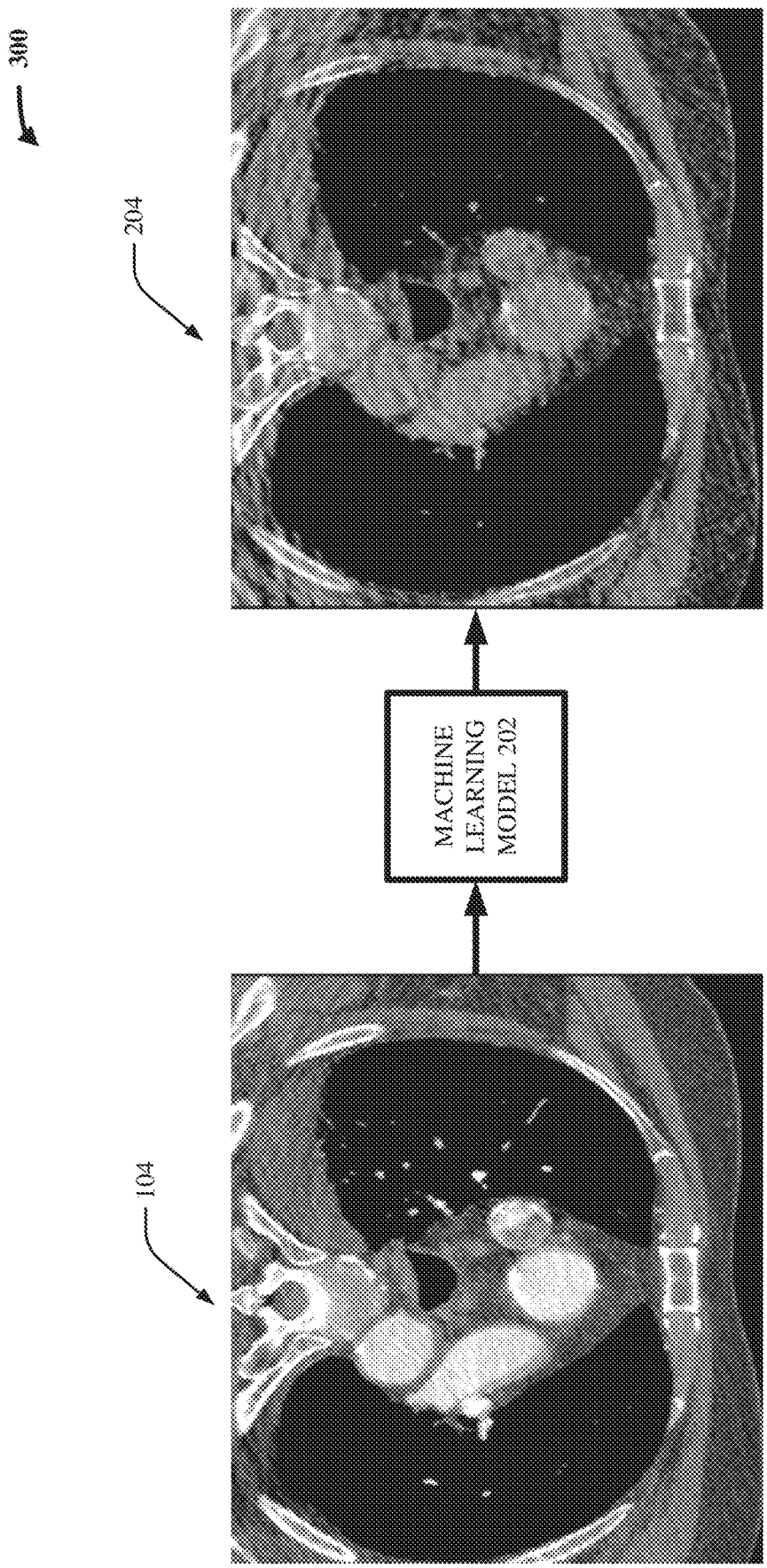
FIG. 3 illustrates an example, non-limiting block diagram showing how a machine learning model as described herein can transform the domain of a medical image in accordance with one or more embodiments described herein.

FIG. 3 illustrates an example, non-limiting block diagram 300 showing how the machine learning model 202 can transform the domain of the medical image 104 in accordance with one or more embodiments described herein.

In the non-limiting example shown in FIG. 3, the medical image 104 can be an axial CT image depicting a patient's chest cavity and heart, that was captured/generated at an electrical energy level of 70 kVp. That is, the first medical scanning domain 106 in this non-limiting example can be an electrical energy level of 70 kVp. Those having ordinary skill in the art will recognize that the HU intensity distribution of the medical image 104, as shown in FIG. 3, looks and/or appears to be consistent with an electrical energy level of 70 kVp.

In various aspects, it can be desired to approximate and/or estimate what the medical image 104 would have looked like if it had instead been captured/generated at 120 kVp. Accordingly, the machine learning model 202 can be configured and/or trained (as described in more detail below with respect to FIGS. 8-9) to transform and/or convert CT scans taken at 70 kVp to CT scans taken at 120 kVp. Thus, in various cases, the transformation component 114 can feed the medical image 104 to the machine learning model 202 as input, and the machine learning model 202 can produce as output the predicted image 204. As shown in FIG. 3, the predicted image 204 can visually depict the same axial view of the chest cavity and heart of the patient as the medical image 104, but the predicted image 204 can look and/or appear to have been captured/generated at an electrical energy level of 120 kVp rather than at an electrical energy level of 70 kVp. That is, the second medical scanning domain 206 in this non-limiting example can be an electrical energy level of 120 kVp. In other words, the predicted image 204 that is shown in FIG. 3 can be considered as representing how the medical image 104 depicting the patient's chest cavity and heart would have looked if the medical image 104 had been originally captured/generated at 120 kVp. Those having ordinary skill in the art will recognize that the HU intensity distribution of the predicted image 204, as shown in FIG. 3, looks and/or appears to be consistent with an electrical energy level of 120 kVp.

In current clinical practice, a CT image that is captured/generated at 70 kVp can be considered as a low-power and/or low-dose CT scan, whereas a CT image that is captured/generated at 120 kVp can be considered as a high-power and/or high-dose CT scan. Exposing a patient to a low-power and/or low-dose CT scan can be safer from the perspective of the patient's health (e.g., less exposure to cancer-causing radiation) but can be suboptimal from the perspective of diagnosis/prognosis (e.g., a low-power and/or low-dose CT scan can exhibit decreased visual quality; preferred/desired diagnostic techniques cannot be reliably applied to a low-power and/or low-dose CT scan). On the other hand, exposing a patient to a high-power and/or high-dose CT scan can be desirable from the perspective of diagnosis/prognosis (e.g., a high-power and/or high-dose CT scan can exhibit increased visual quality; preferred/desired diagnostic techniques can be reliably applied to a high-power and/or high-dose CT scan) but can be suboptimal from the perspective of the patient's health (e.g., increased exposure to cancer-causing radiation). Existing techniques in clinical practice offer no solution to resolve this conflict.

Various embodiments of the subject innovation, on the other hand, can address this problem. Specifically, a low-power/low-dose CT scan (e.g., medical image 104) can be captured/generated from the patient, and such low-power/low-dose CT scan can be fed as input to the machine learning model 202. This can cause the machine learning model 202 to produce as output an image (e.g., predicted image 204) that estimates and/or represents how the low-power/low-dose CT scan would have looked if it had instead been originally captured/generated as a high-power/high-dose CT scan. In this way, the patient is not exposed to excessively high amounts of radiation, and yet an image that estimates and/or approximates a high-power/high-dose CT scan of the patient is nevertheless ultimately obtained for purposes of diagnosis and/or prognosis. This certainly constitutes a concrete and tangible technical improvement in the field of medical imaging.

Those having ordinary skill in the art will appreciate that FIG. 3 illustrates a mere non-limiting example where the machine learning model 202 is configured and/or trained to transform and/or convert CT images from an electrical energy level of 70 kVp to an electrical energy level of 120 kVp. In various other embodiments, the machine learning model 202 can be configured and/or trained to transform and/or convert CT images from any electrical energy level to any other electrical energy level. In still other embodiments, the machine learning model 202 can be configured and/or trained to transform and/or convert CT images from any contrast phase to any other contrast phase. In yet other embodiments, the machine learning model 202 can be configured and/or trained to transform and/or convert CT images from any energy-contrast pair to any other energy-contrast pair. That is, those having ordinary skill in the art will understand that the machine learning model 202 can be configured and/or trained to transform and/or convert a CT image from any suitable CT scanning domain to any other suitable CT scanning domain, as desired. Moreover, in various aspects, those having ordinary skill in the art will appreciate that the machine learning model 202 can be configured to operate on any other suitable type of medical image (e.g., MRI, X-ray, PET, ultrasound) and not just CT images.

Figure 4:
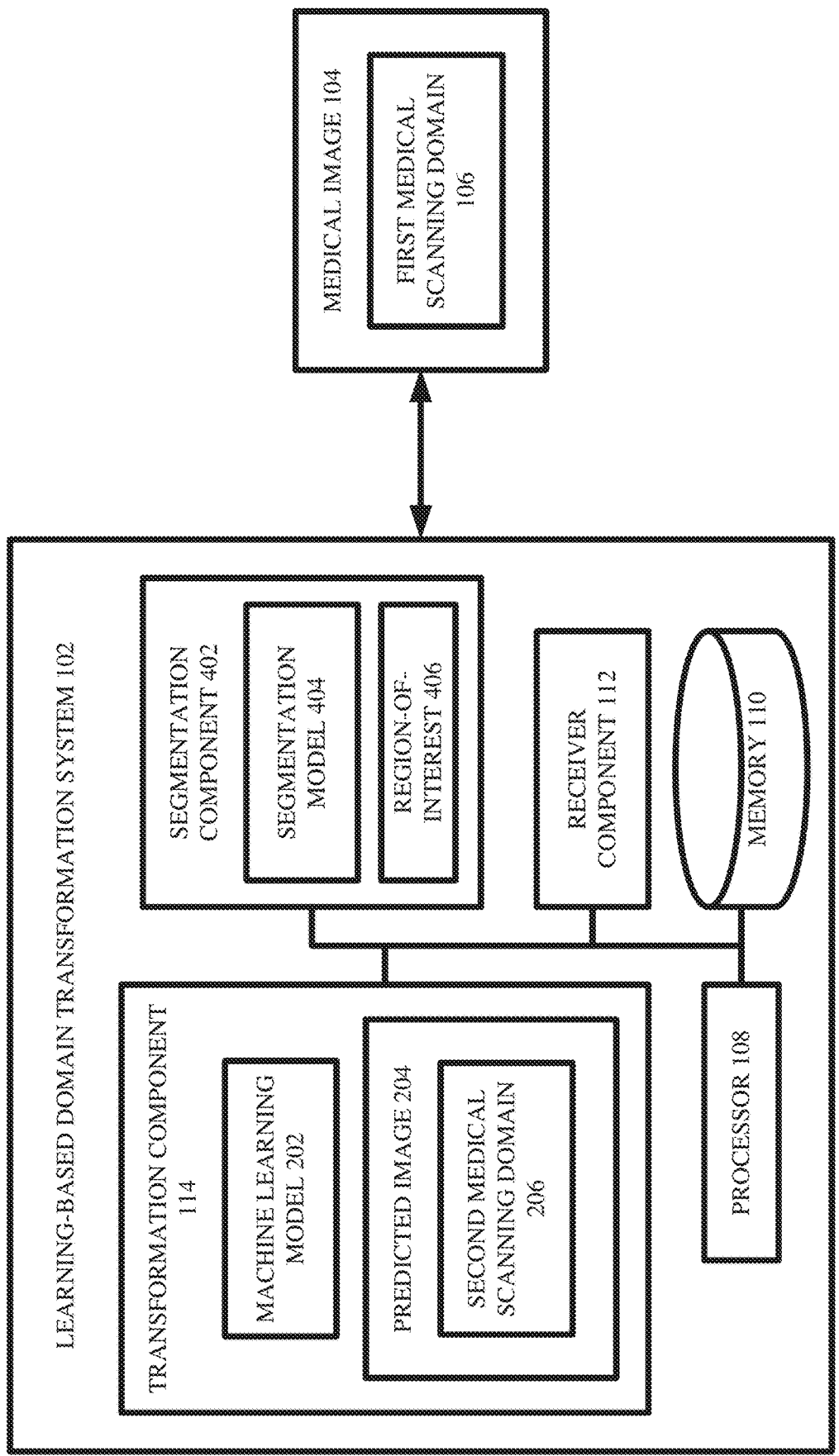
FIG. 4 illustrates a block diagram of an example, non-limiting system including a segmentation model that facilitates learning-based domain transformation for medical images in accordance with one or more embodiments described herein.

FIG. 4 illustrates a block diagram of an example, non-limiting system 400 including a segmentation model that can facilitate learning-based domain transformation for medical images in accordance with one or more embodiments described herein. As shown, the system 400 can, in some cases, comprise the same components as the system 200, and can further comprise a segmentation component 402.

In various embodiments, the segmentation component 402 can electronically store, electronically maintain, electronically control, and/or otherwise electronically access a segmentation model 404. In various instances, the segmentation component 402 can electronically execute the segmentation model 404 on the medical image 104, which can cause the segmentation model 404 to identify a region-of-interest 406 that is depicted within the medical image 104. In various cases, the region-of-interest 406 can be any suitable portion (e.g., any suitable subset of pixels/voxels) of the medical image 104, that is deemed and/or considered to be medically important for purposes of diagnosis/prognosis. As an example, the region-of-interest 406 can include the anatomical structure that is depicted in the medical image 104 and can exclude background portions of the medical image 104. As another example, the region-of-interest 406 can include a portion of the anatomical structure that is depicted in the medical image 104 and can exclude both a remainder of the anatomical structure and background portions of the medical image 104. In various aspects, the segmentation model 404 can exhibit any suitable artificial intelligence architecture. For example, the segmentation model 404 can be a deep learning segmentation model (e.g., including any suitable number of layers, any suitable numbers of neurons in various layers, any suitable activation functions, and/or any suitable connectivity patterns). Moreover, in various instances, the segmentation model 404 can be trained to identify the region-of-interest 406 via any suitable training paradigm (e.g., supervised learning, unsupervised learning, reinforcement learning).

In various aspects, once the segmentation model 404 has identified the region-of-interest 406 within the medical image 104, the segmentation component 402 can electronically crop the medical image 104, such that the medical image 104 now contains only the region-of-interest 406 and no longer contains the background portions and/or regions-of-disinterest. In other words, the segmentation component 402 can eliminate and/or delete any pixels/voxels of the medical image 104 that do not make up the region-of-interest 406, and the segmentation component 402 can refrain from eliminating/deleting any pixels/voxels of the medical image 104 that do make up the region-of-interest 406. In any case, the segmentation component 402 can cause the medical image 104 to depict only and/or substantially only the region-of-interest 406. Accordingly, the transformation component 114 can execute the machine learning model 202 on the region-of-interest 406 (e.g., on the cropped version of the medical image 104), thereby yielding the predicted image 204. Those having ordinary skill in the art will appreciate that, in such cases, the predicted image 204 can have the same dimensionality as the region-of-interest 406 (e.g., can the same number and/or arrangement of pixels/voxels as the cropped version of the medical image 104).

Figure 5:
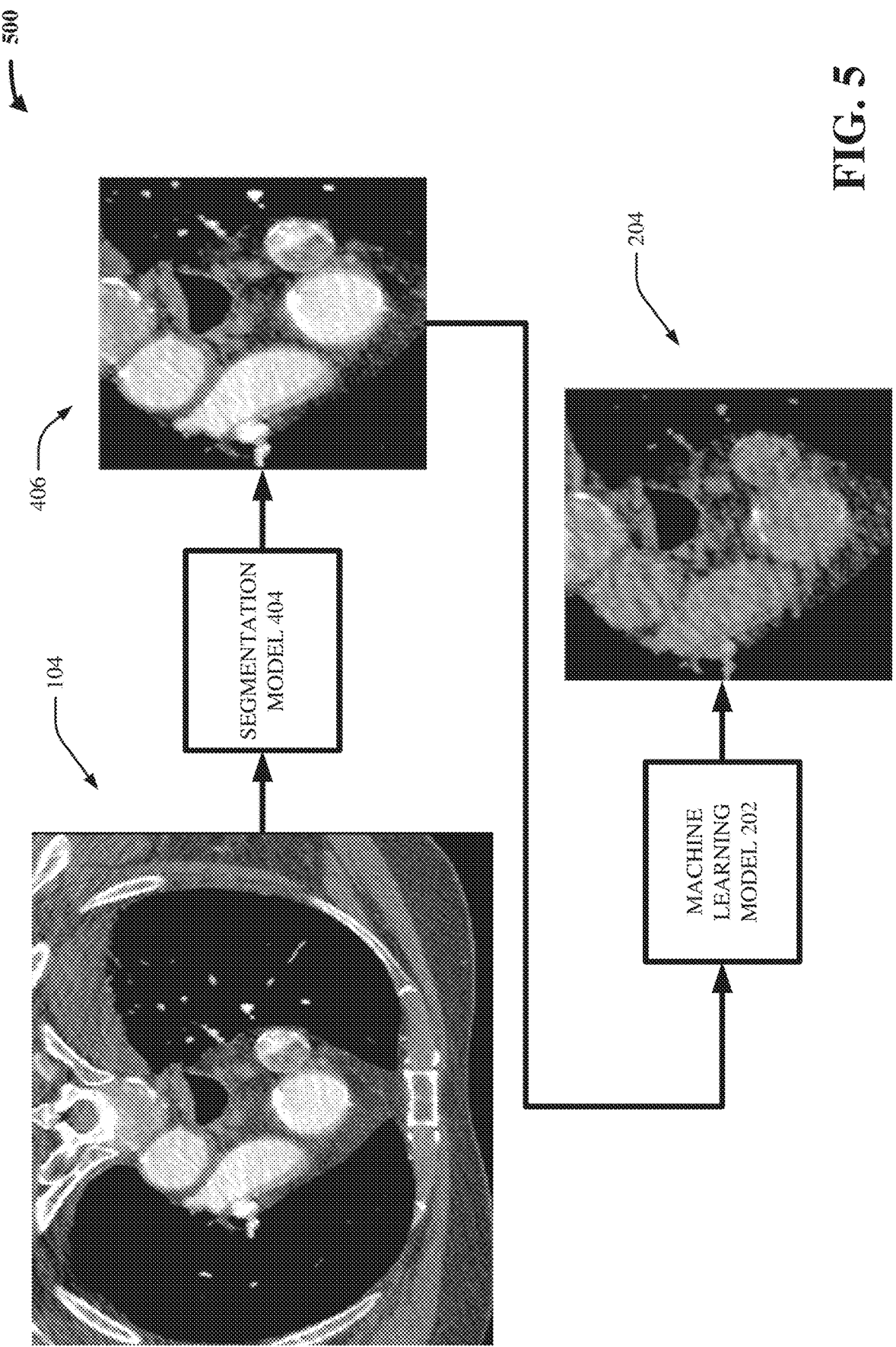
FIG. 5 illustrates an example, non-limiting block diagram showing how a segmentation model and a machine learning model as described herein can transform the domain of a medical image in accordance with one or more embodiments described herein.

FIG. 5 illustrates an example, non-limiting block diagram 500 showing how the segmentation model 404 and the machine learning model 202 can transform the domain of the medical image 104 in accordance with one or more embodiments described herein.

As shown in the non-limiting example of FIG. 5, the medical image 104 can be an axial CT image depicting a patient's chest cavity and heart, that was captured/generated at an electrical energy level of 70 kVp. That is, the medical image 104 of FIG. 5 can be the same as the medical image 104 of FIG. 3. In various aspects, the segmentation component 402 can execute the segmentation model 404 on the medical image 104, thereby causing the segmentation model 404 to identify the region-of-interest 406 within the medical image 104. Moreover, the segmentation component 402 can crop out background portions of the medical image 104, such that only the region-of-interest 406 remains in the cropped version of the medical image 104. As shown in FIG. 5, the region-of-interest 406 in this non-limiting example can include the heart that is depicted in the medical image 104 and can exclude the surrounding chest cavity (e.g., the ribs and vertebrae) that is depicted around in the heart in the medical image 104.

Note that, at this point, the region-of-interest 406 (e.g., the cropped version of the medical image 104) can still exhibit an HU intensity distribution that corresponds to an electrical energy level of 70 kVp. Accordingly, in various embodiments, the transformation component 114 can execute the machine learning model 202 on the region-of-interest 406

(e.g., on the cropped version of the medical image 104), thereby causing the machine learning model 202 to output the predicted image 204. As shown, in various cases, the predicted image 204 can depict the same view of the heart as the region-of-interest 406 (e.g., as the cropped version of the medical image 104), but the predicted image 204 can look and/or appear to have been captured/generated at an electrical energy level of 120 kVp instead of 70 kVp. Those having ordinary skill in the art will appreciate that, in such cases, the predicted image 204 can have the same dimensionality as the region-of-interest 406 (e.g., as the cropped version of the medical image 104), rather than the full medical image 104. Furthermore, those having ordinary skill in the art will appreciate that, by configuring the machine learning model 202 to operate/execute on the region-of-interest 406 (e.g., on the cropped version of the medical image 104) rather than on the entirety of the medical image 104, the machine learning model 202 can avoid getting slowed down and/or distracted by background portions of the medical image 104. That is, when cropping by the segmentation component 402 is implemented, the machine learning model 202 can achieve better performance.

Figure 6:
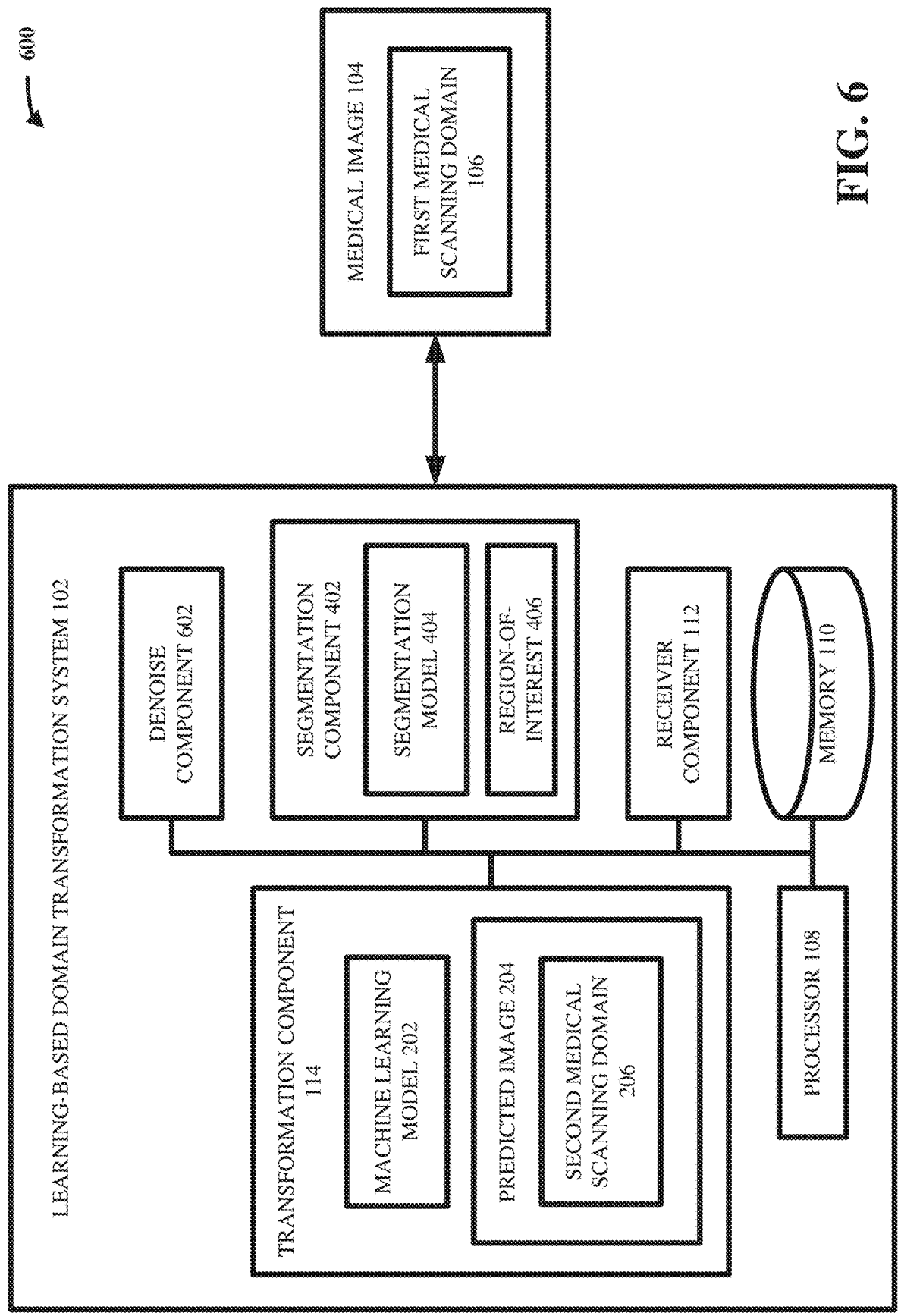
FIG. 6 illustrates a block diagram of an example, non-limiting system including a denoise component that facilitates learning-based domain transformation for medical images in accordance with one or more embodiments described herein.

FIG. 6 illustrates a block diagram of an example, non-limiting system 600 including a denoise component that can facilitate learning-based domain transformation for medical images in accordance with one or more embodiments described herein. As shown, the system 600 can, in some cases, comprise the same components as the system 400, and can further comprise a denoise component 602.

In various embodiments, the denoise component 602 can electronically apply one or more denoising techniques to the medical image 104, prior to the execution of the machine learning model 202. More specifically, in various aspects, the denoise component 602 can electronically measure and/or otherwise electronically determine a level of noise exhibited by the medical image 104. If the level of noise is lesser than any suitable threshold, the denoise component 602 can refrain from taking further action. In such case, the segmentation component 402 can identify the region-of-interest 406 in the medical image 104 and can crop the medical image 104 accordingly, and the transformation component 114 can execute the machine learning model 202 on the region-of-interest 406 (e.g., on the cropped version of the medical image 104). On the other hand, if the level of noise is greater than any suitable threshold, the denoise component 602 can apply the one or more denoising techniques to the medical image 104, thereby reducing the level of noise of the medical image 104. In such case, the segmentation component 402 can identify the region-of-interest 406 in the denoised version of the medical image 104 and can crop the denoised version of the medical image 104 accordingly, and the transformation component 114 can execute the machine learning model 202 on the region-of-interest 406 (e.g., on the denoised and cropped version of the medical image 104).

Those having ordinary skill in the art will appreciate that the denoise component 602 can implement any suitable denoising techniques as desired (e.g., denoising filters, deep learning denoising models). Those having ordinary skill in the art will further appreciate that the denoise component 602 can, in some embodiments, apply the one or more denoising techniques after the segmentation component 402 crops the medical image 104. That is, the denoise component 602 can evaluate the noise level of the cropped version of the medical image 104 and apply the one or more denoising techniques to the cropped version of the medical image 104 accordingly. In any case, the denoise component 602 can ensure, prior to execution of the machine learning model 202, that the medical image 104 (e.g., that the cropped version of the medical image 104) does not exhibit excessive noise. This can allow the machine learning model 202 to achieve higher performance accuracy upon execution.

Figure 7:
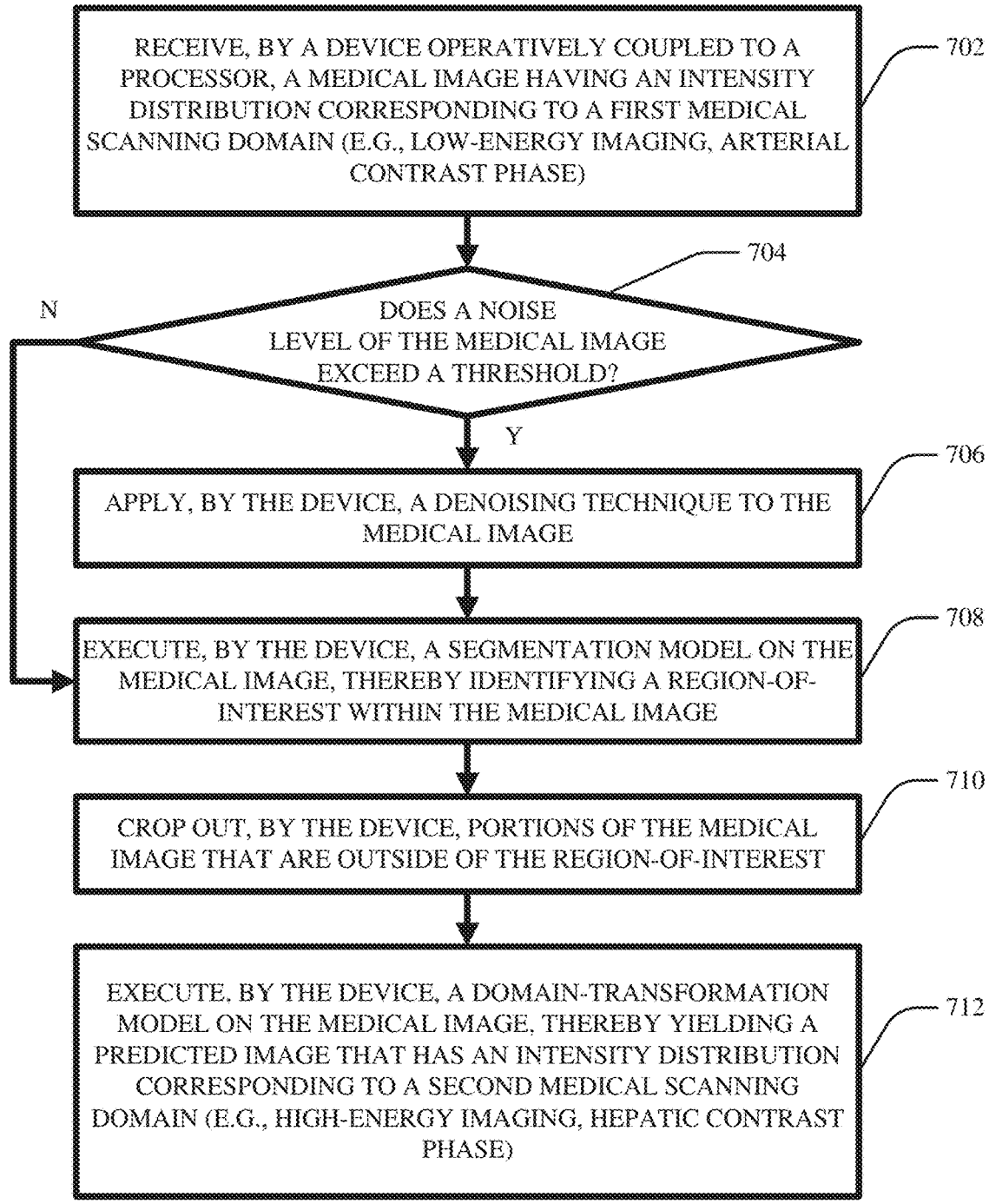
FIG. 7 illustrates a flow diagram of an example, non-limiting computer-implemented method that facilitates learning-based domain transformation for medical images in accordance with one or more embodiments described herein.

FIG. 7 illustrates a flow diagram of an example, non-limiting computer-implemented method 700 that can facilitate learning-based domain transformation for medical images in accordance with one or more embodiments described herein. In various cases, the learning-based domain transformation system 102 can facilitate the computer-implemented method 700.

In various embodiments, act 702 can include receiving, by a device (e.g., 112) operatively coupled to a processor, a medical image (e.g., 104) having an intensity distribution corresponding to a first medical scanning domain (e.g., 106). As an example, the first medical scanning domain can be a low electrical energy level and/or a particular contrast phase (e.g., arterial contrast phase).

In various aspects, act 704 can include determining, by the device (e.g., 602), whether a noise level of the medical image exceeds a threshold. If so, the computer-implemented method 700 can proceed to act 706. If not, the computer-implemented method 700 can proceed to act 708.

In various instances, act 706 can include applying, by the device (e.g., 602), a denoising technique to the medical image. This can ensure that the medical image does not exhibit excessive noise that might otherwise confound down-stream analysis.

In various cases, act 708 can include executing, by the device (e.g., 402), a segmentation model (e.g., 404) on the medical image, thereby identifying a region-of-interest (e.g., 406) within the medical image.

In various aspects, act 710 can include cropping out, by the device (e.g., 402), portions of the medical image that are outside of the region-of-interest. This can ensure that the medical image no longer includes unimportant parts that might otherwise confound downstream analysis.

In various instances, act 712 can include executing, by the device (e.g., 114), a domain-transformation model (e.g., 202) on the medical image, thereby yielding a predicted image (e.g., 204) that has an intensity distribution corresponding to a second medical scanning domain (e.g., 206). As an example, if the first medical scanning domain is a low electrical energy level (e.g., 70 kVp), then the second medical scanning domain can be a high electrical energy level (e.g., 120 kVp). As another example, if the first medical scanning domain is a particular contrast phase (e.g., arterial phase), then the second medical scanning domain can be a different contrast phase (e.g., hepatic phase).

In various aspects, FIGS. 1-7 and associated text can be considered as describing how the machine learning model 202 functions during inferencing. However, before the machine learning model 202 can be deployed and/or inferenced, the machine learning model 202 should be trained. Such training is described with respect to FIGS. 8-9.

Figure 8:
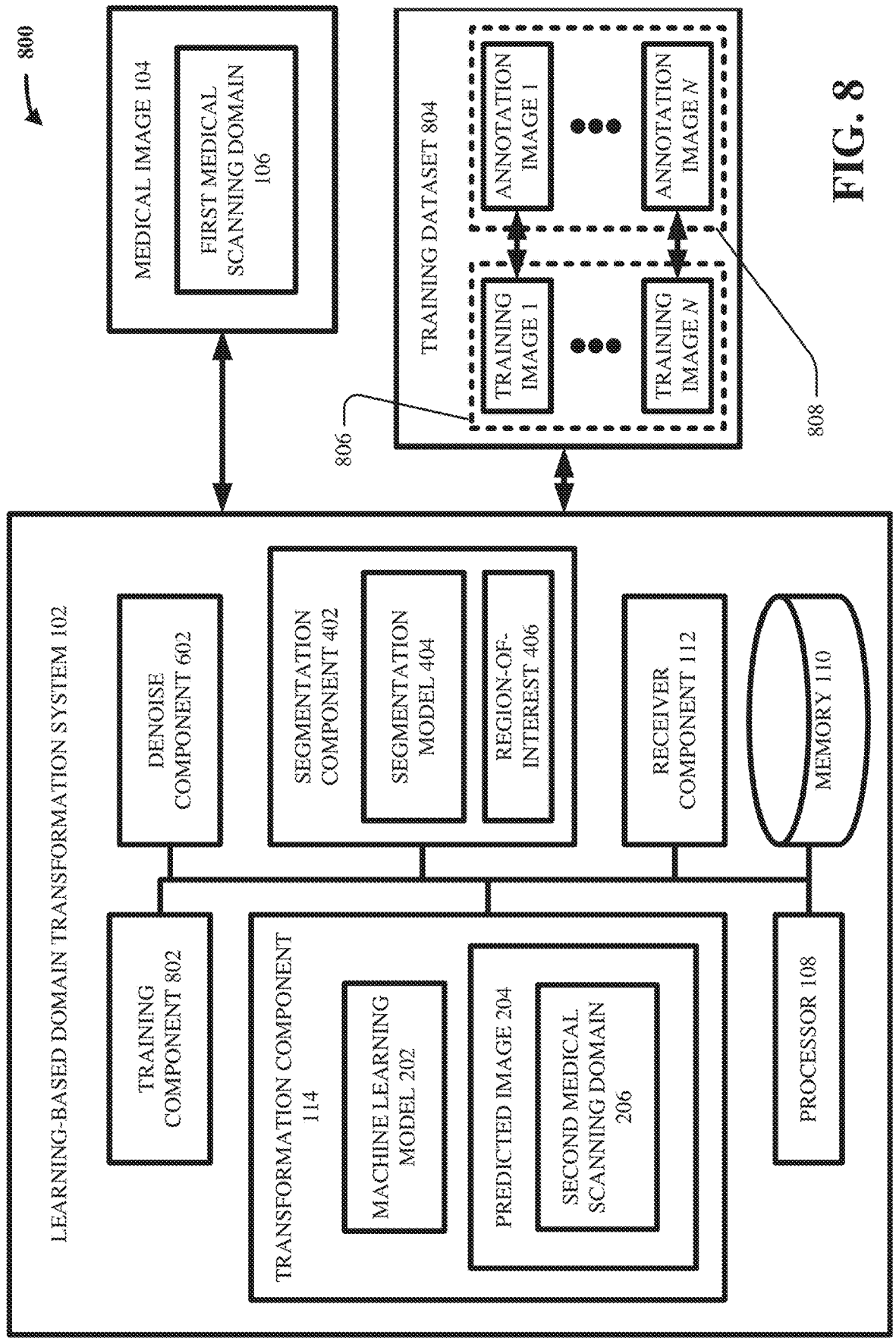
FIG. 8 illustrates a block diagram of an example, non-limiting system including a training component that facilitates learning-based domain transformation for medical images in accordance with one or more embodiments described herein.

FIG. 8 illustrates a block diagram of an example, non-limiting system 800 including a training component that can facilitate learning-based domain transformation for medical images in accordance with one or more embodiments described herein. As shown, the system 800 can, in some cases, comprise the same components as the system 600, and can further comprise a training component 802 and/or a training dataset 804.

In various embodiments, the receiver component 112 can electronically receive, retrieve, and/or access the training dataset 804 from any suitable database, data structure, and/or computing device (not shown). In various aspects, the training component 802 can leverage the training dataset 804 to train the machine learning model 202 to accurately transform/convert the first medical scanning domain 106 to the second medical scanning domain 206, as described more thoroughly below.

In various instances, the training dataset 804 can include a set of training images 806 and a set of annotation images 808. In various aspects, the set of training images 806 can include any suitable number of training images. For instances, the set of training images 806 can include n training images, for any suitable positive integer n (e.g., training image 1 to training image n). In various cases, the set of annotation images 808 can respectively correspond to the set of training images 806. That is, if the set of training images 806 has n training images, then the set of annotation images 808 can have n annotation images (e.g., annotation image 1 to annotation image n). In other words, there can be one unique annotation image per training image. For example, in various instances, the set of training images 806 can include a training image 1, and the set of annotation images 808 can likewise include an annotation image 1 that corresponds to the training image 1. Moreover, the set of training images 806 can include a training image n, and the set of annotation images 808 can likewise include annotation image n that corresponds to the training image n. In various cases, each of the training images 806 can have the same format and/or dimensionality as the medical image 104. Moreover, each of the training images 806 can have been captured/generated according to the first medical scanning domain 106. In stark contrast, each of the set of annotation images 808 can have been captured/generated according to the second medical scanning domain 206.

More specifically, consider the training image 1 and the annotation image 1. In various aspects, the training image 1 can depict one or more particular anatomical structures according to the first medical scanning domain 106. In various instances, the annotation image 1 can depict the same one or more particular anatomical structures as the training image 1, but the annotation image 1 can do so according to the second medical scanning domain 206. In other words, the training image 1 can be a medical scan that is captured/generated via the first medical scanning domain 106, and the annotation image 1 can be a known ground-truth image that represents how the training image 1 should look and/or should visually appear if it had been captured/generated via the second medical scanning domain 206. Similarly, consider the training image n and the annotation image n. In various aspects, the training image n can depict one or more certain anatomical structures according to the first medical scanning domain 106. In various instances, the annotation image n can depict the same one or more certain anatomical structures as the training image n, but the annotation image n can do so according to the second medical scanning domain 206. That is, the training image n can be a medical scan that is captured/generated via the first medical scanning domain 106, and the annotation image n can be a known ground-truth image that represents how the training image n should look and/or should visually appear if it had been captured/generated via the second medical scanning domain 206.

In various aspects, each of the set of training images 806 can be respectively registered/aligned with corresponding ones of the set of annotation images 808. That is, the training image 1 can be registered and/or aligned in a pixel-to-pixel (and/or voxel-to-voxel) fashion with the annotation image 1, and the training image n can be registered and/or aligned in a pixel-to-pixel (and/or voxel-to-voxel) fashion with the annotation image n. In some cases, such registration/alignment can be facilitated at time of capture/generation of the training dataset 804 (e.g., via dual-energy scanning modalities). In other cases, such registration/alignment can be facilitated by the training component 802. For example, the training component 802 can iteratively perturb (e.g., rotate and/or translate) the training image 1 and/or the annotation image 1 until pixel-wise (voxel-wise) alignment is achieved between the training image 1 and the annotation image 1. Similarly, the training component 802 can iteratively perturb (e.g., rotate and/or translate) the training image n and/or the annotation image n until pixel-wise (voxel-wise) alignment is achieved between the training image n and the annotation image n. As yet another example, the training component 802 can implement a pre-trained registration/alignment model (e.g., a deep learning model) to facilitate such registration/alignment.

In embodiments where the segmentation component 402 and the denoise component 602 are not implemented, the training component 802 can train the machine learning model 202 as follows. The internal parameters (e.g., weights, biases) of the machine learning model 202 can be initialized in any suitable fashion (e.g., random initialization). In various instances, the training component 802 can select a training image from the set of training images 806, and the training component 802 can also select an annotation image from the set of annotation images 808 that corresponds to the selected training image (e.g., the annotation image 1 corresponds to the training image 1). In various cases, the transformation component 114 can feed the selected training image to the machine learning model 202. The selected training image can complete a forward pass through the machine learning model 202, which can cause the machine learning model 202 to output a predicted image based on the selected training image (e.g., the predicted image can have the same number and/or arrangement of pixels/voxels as the selected training image). In various aspects, the predicted image can be considered as representing how the machine learning model 202 believes that the selected training image would look if it had been captured/generated via the second medical scanning domain 206. On the other hand, the selected annotation image can represent how the selected training image is actually known to look when captured/generated via the second medical scanning domain 206. Accordingly, the training component 802 can compute an error/loss between the predicted image and the selected annotation image. In various cases, any suitable error/loss function can be implemented (e.g., any suitable weights and/or constraints can be utilized as desired). Thus, the training component 802 can update, via backpropagation, the internal parameters of the machine learning model 202 based on the computed error/loss. In various cases, the training component 802 can repeat this procedure for each training image in the set of training images 806, with the ultimate result being that the internal parameters of the machine learning model 202 become iteratively optimized. As those having ordinary skill in the art will appreciate, the training component 802 can implement any other suitable training batch sizes and/or any suitable number of training epochs.

In embodiments where the segmentation component 402 is implemented but where the denoise component 602 is not implemented, the training component 802 can train the machine learning model 202 as follows. The internal parameters of the machine learning model 202 can be initialized in any suitable fashion. In various instances, the training component 802 can select a training image from the set of training images 806, and the training component 802 can also select an annotation image from the set of annotation images 808 that corresponds to the selected training image. In various cases, the segmentation component 402 can execute the segmentation model 404 on the selected training image and/or on the selected annotation image. This can cause the segmentation model 404 to identify a region-of-interest in the selected training image and to identify the same region-of-interest in the selected annotation image. Thus, the segmentation component 402 can crop out of the selected training image any pixels/voxels that are not within the region-of-interest. Likewise, the segmentation component 402 can crop out of the selected annotation image any pixels/voxels that are not within the region-of-interest. In various aspects, the transformation component 114 can feed the cropped version of the selected training image to the machine learning model 202. The cropped version of the selected training image can complete a forward pass through the machine learning model 202, which can cause the machine learning model 202 to output a predicted image based on the cropped version of the selected training image (e.g., the predicted image can have the same number and/or arrangement of pixels/voxels as the cropped version of the selected training image). In various aspects, the predicted image can be considered as representing how the machine learning model 202 believes that the cropped version of the selected training image would look if it had been captured/generated via the second medical scanning domain 206. On the other hand, the cropped version of the selected annotation image can represent how the cropped version of the selected training image is actually known to look when captured/generated via the second medical scanning domain 206. Accordingly, the training component 802 can compute an error/loss between the predicted image and the cropped version of the selected annotation image. In various cases, any suitable error/loss function can be implemented. Thus, the training component 802 can update, via backpropagation, the internal parameters of the machine learning model 202 based on the computed error/loss. In various cases, the training component 802 can repeat this procedure for each training image in the set of training images 806, with the ultimate result being that the internal parameters of the machine learning model 202 become iteratively optimized. As those having ordinary skill in the art will appreciate, the training component 802 can implement any other suitable training batch sizes and/or any suitable number of training epochs.

In embodiments where the segmentation component 402 and the denoise component 602 are implemented, the training component 802 can train the machine learning model 202 as follows. The internal parameters of the machine learning model 202 can be initialized in any suitable fashion. In various instances, the training component 802 can select a training image from the set of training images 806, and the training component 802 can also select an annotation image from the set of annotation images 808 that corresponds to the selected training image. In various cases, the denoise component 602 can apply a denoising technique to the selected training image if a noise level of the selected training image exceeds any suitable margin. Similarly, the denoise component 602 can apply a denoising technique to the selected annotation image if a noise level of the selected annotation image exceeds any suitable margin. In various instances, the segmentation component 402 can execute the segmentation model 404 on the denoised version of the selected training image and/or on the denoised version of the selected annotation image. This can cause the segmentation model 404 to identify a region-of-interest in the denoised version of the selected training image and to identify the same region-of-interest in the denoised version of the selected annotation image. Thus, the segmentation component 402 can crop out of the denoised version of the selected training image any pixels/voxels that are not within the region-of-interest. Likewise, the segmentation component 402 can crop out of the denoised version of the selected annotation image any pixels/voxels that are not within the region-of-interest. In various aspects, the transformation component 114 can feed the cropped and denoised version of the selected training image to the machine learning model 202. The cropped and denoised version of the selected training image can complete a forward pass through the machine learning model 202, which can cause the machine learning model 202 to output a predicted image based on the cropped and denoised version of the selected training image (e.g., the predicted image can have the same number and/or arrangement of pixels/voxels as the cropped and denoised version of the selected training image). In various aspects, the predicted image can be considered as representing how the machine learning model 202 believes that the cropped and denoised version of the selected training image would look if it had been captured/generated via the second medical scanning domain 206. On the other hand, the cropped and denoised version of the selected annotation image can represent how the cropped and denoised version of the selected training image is actually known to look when captured/generated via the second medical scanning domain 206. Accordingly, the training component 802 can compute an error/loss between the predicted image and the cropped and denoised version of the selected annotation image. In various cases, any suitable error/loss function can be implemented. Thus, the training component 802 can update, via backpropagation, the internal parameters of the machine learning model 202 based on the computed error/loss. In various cases, the training component 802 can repeat this procedure for each training image in the set of training images 806, with the ultimate result being that the internal parameters of the machine learning model 202 become iteratively optimized. As those having ordinary skill in the art will appreciate, the training component 802 can implement any other suitable training batch sizes and/or any suitable number of training epochs.

Figure 9:
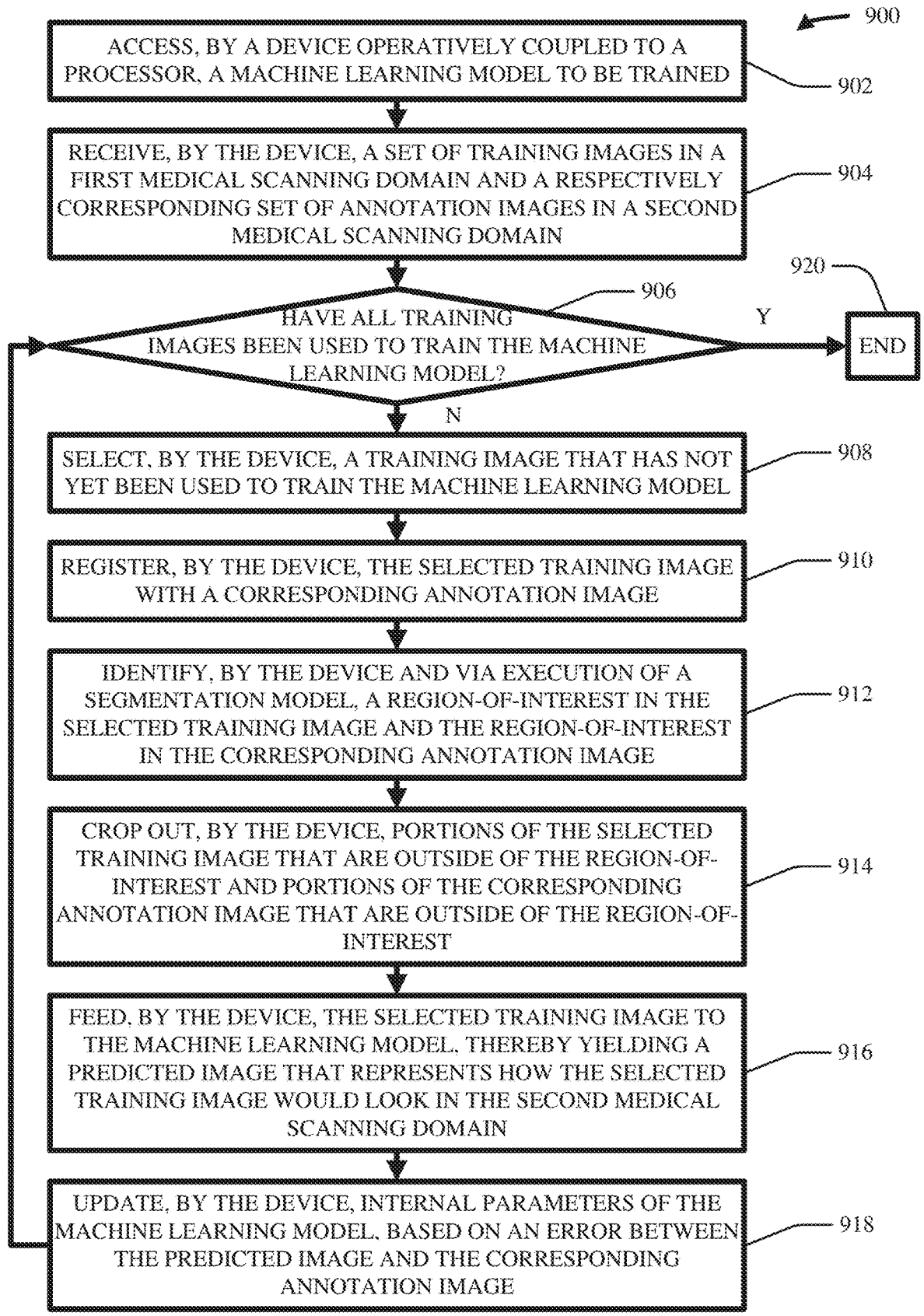
FIG. 9 illustrates a flow diagram of an example, non-limiting computer-implemented method that facilitates training of a domain transformation machine learning model in accordance with one or more embodiments described herein.

FIG. 9 illustrates a flow diagram of an example, non-limiting computer-implemented method 900 that can facilitate training of a domain transformation machine learning model in accordance with one or more embodiments described herein. In various cases, the learning-based domain transformation system 102 can facilitate the computer-implemented method 900.

In various embodiments, act 902 can include accessing, by a device (e.g., 112) operatively coupled to a processor, a machine learning model (e.g., 202) to be trained.

In various aspects, act 904 can include receiving, by the device (e.g., 112), a set of training images (e.g., 806) in a first medical scanning domain (e.g., 106) and a respectively corresponding set of annotation images (e.g., 808) in a second medical scanning domain (e.g., 206).

In various instances, act 906 can include determining, by the device (e.g., 802), whether all training images in the set have been used to training the machine learning model. If so, the computer-implemented method 900 can proceed to act 920, where the computer-implemented method 900 can end. If not, the computer-implemented method 900 can proceed to act 908.

In various cases, act 908 can include selecting, by the device (e.g., 802), a training image that has not yet been used to train the machine learning model.

In various aspects, act 910 can include registering and/or aligning, by the device (e.g., 802), the selected training image with a corresponding annotation image.

In various instances, act 912 can include identifying, by the device (e.g., 402) and via execution of a segmentation model (e.g., 404), a region-of-interest in the selected training image and the region-of-interest in the corresponding annotation image.

In various cases, act 914 can include cropping out, by the device (e.g., 402), portions of the selected training image that are outside of the region-of-interest and portions of the corresponding annotation image that are outside of the region-of-interest. As those having ordinary skill in the art will appreciate, the cropped version of the selected training image and the cropped version of the corresponding annotation image can have the same number and/or arrangement of pixels/voxels.

In various aspects, act 916 can include feeding, by the device (e.g., 114), the selected training image (e.g., the cropped version of the selected training image) to the machine learning model, thereby yielding a predicted image. In various cases, the predicted image can represent how the selected training image would look in the second medical scanning domain.

In various instances, act 918 can include updating, by the device (e.g., 802), internal parameters of the machine learning model, based on an error between the predicted image and the corresponding annotation image (e.g., the cropped version of the corresponding annotation image). In various cases, the computer-implemented method 900 can proceed back to act 906.

As shown, acts 906-918 can iterate until all training images have been used to train the machine learning model, or otherwise until any other suitable training termination criterion is achieved (e.g., maximum number of epochs, minimum amount of error).

Figure 10:
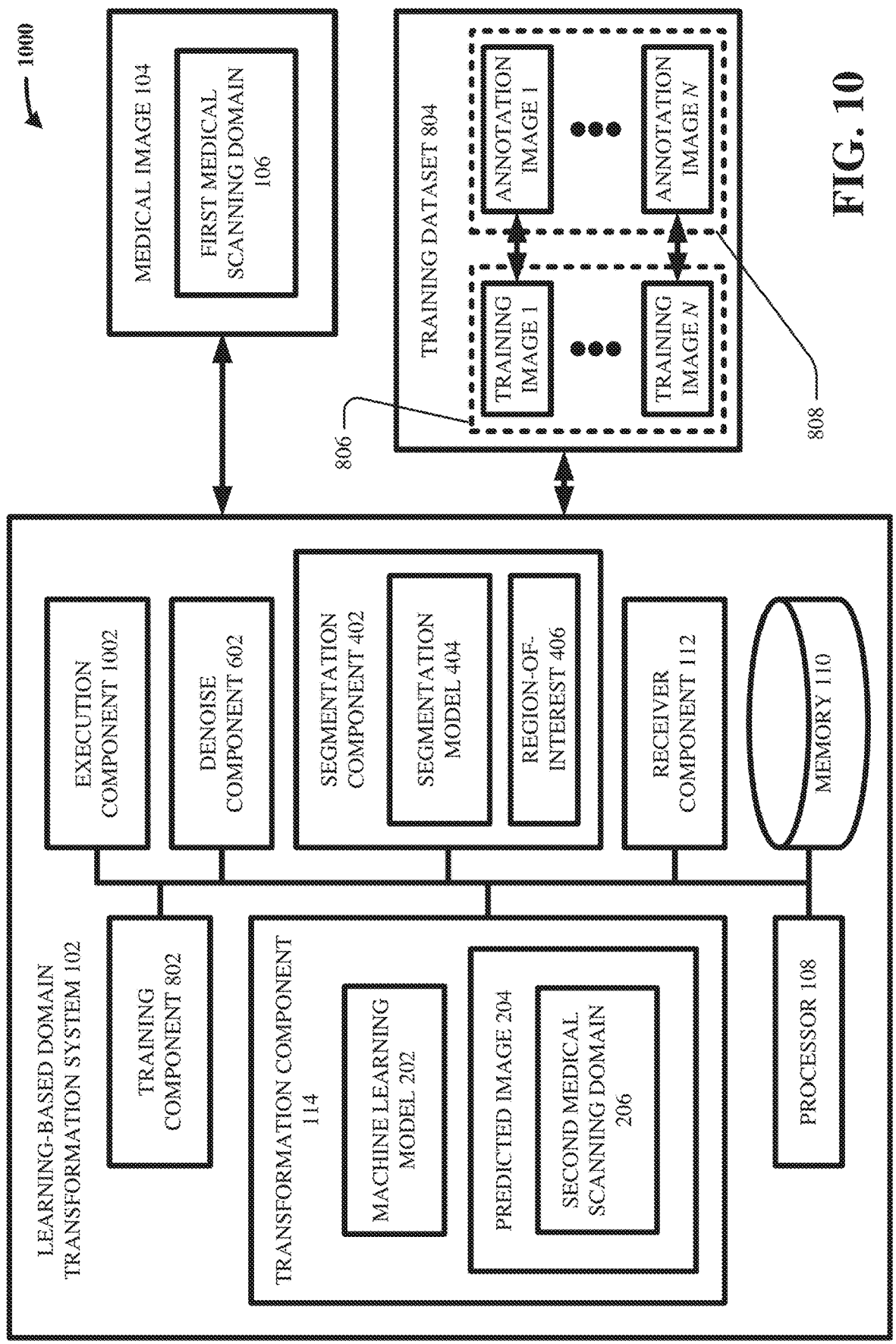
FIG. 10 illustrates a block diagram of an example, non-limiting system including an execution component that facilitates learning-based domain transformation for medical images in accordance with one or more embodiments described herein.

FIG. 10 illustrates a block diagram of an example, non-limiting system 1000 including an execution component that can facilitate learning-based domain transformation for medical images in accordance with one or more embodiments described herein. As shown, the system 1000 can, in some cases, comprise the same components as the system 800, and can further comprise an execution component 1002.

As mentioned above, it can be desired to apply a computerized diagnostic technique (e.g., Agatston scoring) to the medical image 104. But such application can be suboptimal since the computerized diagnostic technique can only be accurately/reliably applied to medical images that are captured/generated via the second medical scanning domain 206. Accordingly, in various embodiments, once the transformation component 114 has produced the predicted image 204, the execution component 1002 can electronically apply and/or execute the computerized diagnostic technique on the predicted image 204. Note that the predicted image 204 can contain the same medically-relevant substantive information as the medical image 104 (e.g., can depict the same anatomical structure as the medical image 104), but the predicted image 204 can appear to have been captured/generated via the second medical scanning domain 206 instead of the first medical scanning domain 106. Thus, the computerized diagnostic technique can be reliably and/or accurately applied to the predicted image 204, thereby yielding medically significant results for the patient. In various cases, the execution component 1002 can electronically transmit such results to any suitable computing device.

Figure 11:
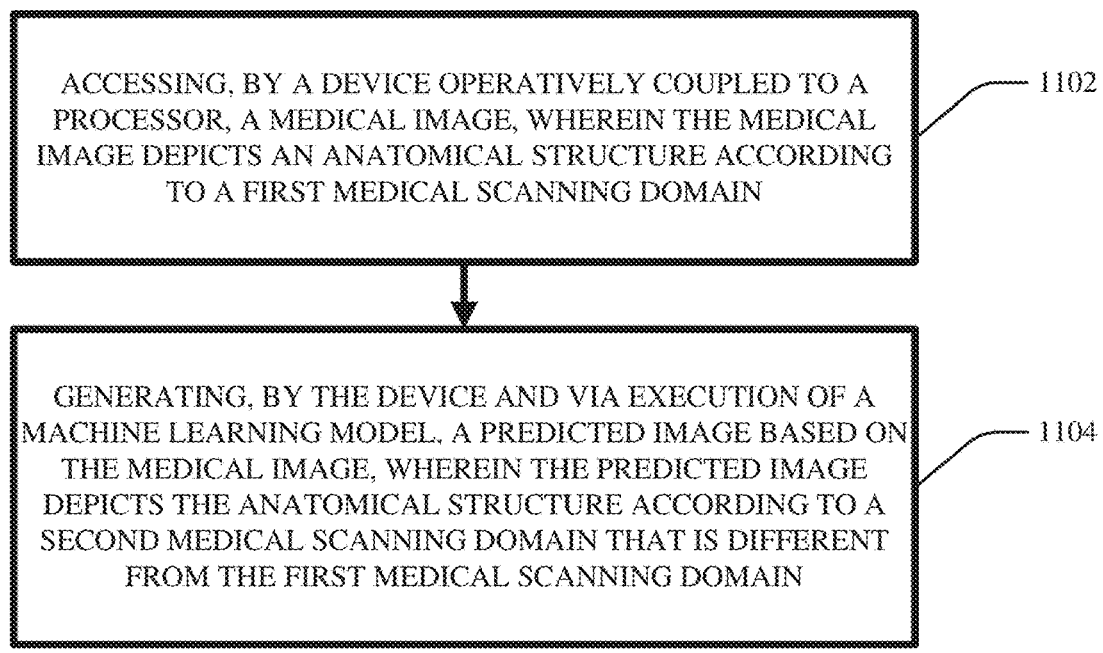
FIG. 11 illustrates a flow diagram of an example, non-limiting computer-implemented method that facilitates learning-based domain transformation for medical images in accordance with one or more embodiments described herein.

FIG. 11 illustrates a flow diagram of an example, non-limiting computer-implemented method 1100 that can facilitate learning-based domain transformation for medical images in accordance with one or more embodiments described herein. In various cases, the learning-based domain transformation system 102 can facilitate the computer-implemented method 1100.

In various embodiments, act 1102 can include accessing, by a device (e.g., 112) operatively coupled to a processor, a medical image (e.g., 104). In various cases, the medical image an depict an anatomical structure according to a first medical scanning domain (e.g., 106).

In various aspects, act 1104 can include generating, by the device (e.g., 114) and via execution of a machine learning model (e.g., 202), a predicted image (e.g., 204) based on the medical image. In various cases, the predicted image an depict the anatomical structure according to a second medical scanning domain (e.g., 206) that is different from the first medical scanning domain.

Although not explicitly shown in FIG. 11, the first medical scanning domain can be a first energy level of a computed tomography (CT) scanning modality, and the second medical scanning domain can be a second energy level of the CT scanning modality that is different from the first energy level.

Although not explicitly shown in FIG. 11, the first medical scanning domain can be a first contrast phase of a computed tomography (CT) scanning modality, and the second medical scanning domain can be a second contrast phase of the CT scanning modality that is different from the first contrast phase.

Although not explicitly shown in FIG. 11, the computer-implemented method 1100 can further comprise: identifying, by the device (e.g., 402) and via execution of a segmentation model (e.g., 404), a region-of-interest (e.g., 406) in the medical image, wherein the generating the predicted image is based on executing the machine learning model on the region-of-interest, and wherein the machine learning model is not executed on a remainder of the medical image.

Although not explicitly shown in FIG. 11, the computer-implemented method 1100 can further comprise: applying, by the device (e.g., 602), one or more denoising techniques to the medical image prior to execution of the machine learning model.

Although not explicitly shown in FIG. 11, the computer-implemented method 1100 can further comprise: training, by the device (e.g., 802), the machine learning model on a training medical image (e.g., training image 1), wherein the training medical image depicts one or more anatomical structures according to the first medical scanning domain, and wherein the training medical image corresponds to a target annotation image (e.g., annotation image 1) that depicts the one or more anatomical structures according to the second medical scanning domain. In various cases, the computer-implemented method 1100 can further include: registering, by the device (e.g., 802), the training medical image with the target annotation image prior to the training.

Various embodiments described herein include a computerized tool that can access a medical image that has been generated/captured via a first medical scanning domain and that can transform and/or convert the medical image into a different medical scanning domain. As explained above, a medical scanning domain can be any suitable configurable setting, configurable control, and/or configurable parameter of a medical imaging device/modality, where changing/adjusting the setting, control, and/or parameter can affect how a medical image visually looks once captured/generated. As a non-limiting example, a medical scanning domain can be an electrical energy level (e.g., capturing CT images at 70 kVp can be considered as one medical scanning domain, while capturing CT images at 120 kVp can be considered as another medical scanning domain). As another non-limiting example, a medical scanning domain can be a contrast phase (e.g., capturing CT images during an early arterial phase can be considered as one medical scanning domain, while capturing CT images during a nephrogenic phase can be considered as another medical scanning domain). Accordingly, when various embodiments of the subject innovation are implemented, a medical image can be captured/generated in one medical scanning domain and can be transformed into another medical scanning domain. This can be particularly useful when the domain is an electrical energy level. For example, a CT image can be captured at a low electrical energy level (e.g., 70 kVp) so that the patient is not exposed to excessive radiation. Then, the CT image can be substantively transformed and/or converted to a high electrical energy level (e.g., 120 kVp), such that diagnostic techniques (e.g., Agatston scoring) that can only be applied to high-dose CT images can be utilized to analyze the CT image. Thus, various embodiments described herein certainly constitute a concrete and tangible technique improvement in the field of medical imaging.

Those having ordinary skill in the art will recognize that the herein-described teachings can be applied to various medical contexts (e.g., transforming CT images from a low electrical energy level to a high electrical energy level can be useful in calcium scoring and/or radiomics; transforming CT images from one contrast phase to another contrast phase can be useful in tissue classification, multi-phase lesion characterization, and/or the creation of virtual non-contrast images).

Those having ordinary skill in the art will appreciate that the herein disclosure describes non-limiting examples of various embodiments of the invention. For ease of description and/or explanation, various portions of the herein disclosure utilize the term "each" when discussing various embodiments of the invention. Those having ordinary skill in the art will appreciate that such usages of the term "each" are non-limiting examples. In other words, when the herein disclosure provides a description that is applied to "each" of some particular computerized object and/or component, it should be understood that this is a non-limiting example of various embodiments of the invention, and it should be further understood that, in various other embodiments of the invention, it can be the case that such description applies to fewer than "each" of that particular computerized object.

To facilitate some of the above-described machine learning aspects of various embodiments of the subject innovation, consider the following discussion of artificial intelligence. Various embodiments of the present innovation herein can employ artificial intelligence (AI) to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z1, z2, z3, z4, zn)$, to a confidence that the input belongs to a class, as by $f(z)=\text{confidence(class)}$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 12:
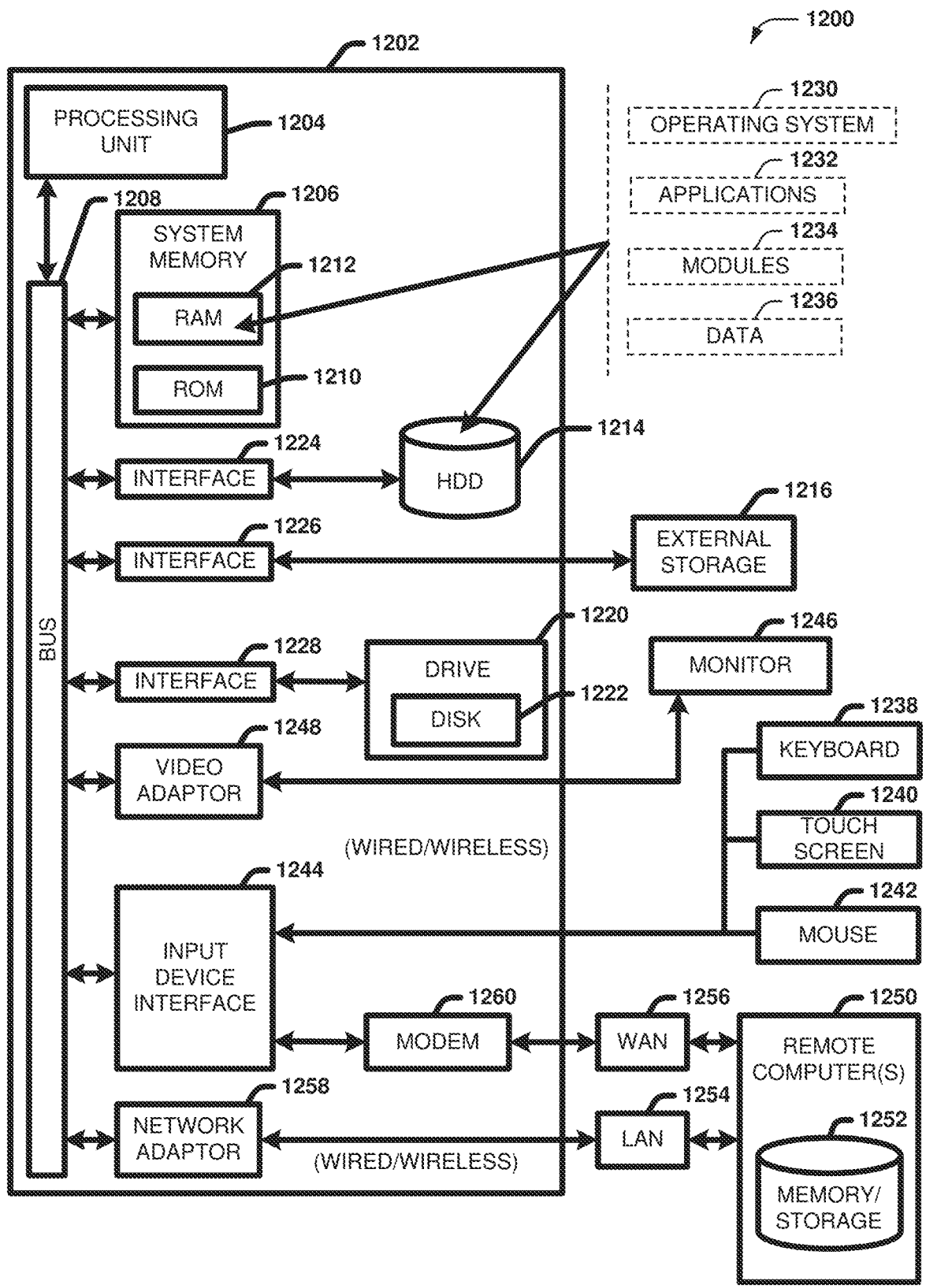
FIG. 12 illustrates a block diagram of an example, non-limiting operating environment in which one or more embodiments described herein can be facilitated.

In order to provide additional context for various embodiments described herein, FIG. 12 and the following discussion are intended to provide a brief, general description of a suitable computing environment 1200 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 12, the example environment 1200 for implementing various embodiments of the aspects described herein includes a computer 1202, the computer 1202 including a processing unit 1204, a system memory 1206 and a system bus 1208. The system bus 1208 couples system components including, but not limited to, the system memory 1206 to the processing unit 1204. The processing unit 1204 can be any of various commercially available processors. Dual microprocessors and other multi processor architectures can also be employed as the processing unit 1204.

The system bus 1208 can be any of several types of bus structure that can further interconnect to a memory bus (with or without a memory controller), a peripheral bus, and a local bus using any of a variety of commercially available bus architectures. The system memory 1206 includes ROM 1210 and RAM 1212. A basic input/output system (BIOS) can be stored in a non-volatile memory such as ROM, erasable programmable read only memory (EPROM), EEPROM, which BIOS contains the basic routines that help to transfer information between elements within the computer 1202, such as during startup. The RAM 1212 can also include a high-speed RAM such as static RAM for caching data.

The computer 1202 further includes an internal hard disk drive (HDD) 1214 (e.g., EIDE, SATA), one or more external storage devices 1216 (e.g., a magnetic floppy disk drive (FDD) 1216, a memory stick or flash drive reader, a memory card reader, etc.) and a drive 1220, e.g., such as a solid state drive, an optical disk drive, which can read or write from a disk 1222, such as a CD-ROM disc, a DVD, a BD, etc. Alternatively, where a solid state drive is involved, disk 1222 would not be included, unless separate. While the internal HDD 1214 is illustrated as located within the computer 1202, the internal HDD 1214 can also be configured for external use in a suitable chassis (not shown). Additionally, while not shown in environment 1200, a solid state drive (SSD) could be used in addition to, or in place of, an HDD 1214. The HDD 1214, external storage device(s) 1216 and drive 1220 can be connected to the system bus 1208 by an HDD interface 1224, an external storage interface 1226 and a drive interface 1228, respectively. The interface 1224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1212, including an operating system 1230, one or more application programs 1232, other program modules 1234 and program data 1236. All or portions of the operating system, applications, modules, and/or data can also be cached in the RAM 1212. The systems and methods described herein can be implemented utilizing various commercially available operating systems or combinations of operating systems.

Computer 1202 can optionally comprise emulation technologies. For example, a hypervisor (not shown) or other intermediary can emulate a hardware environment for operating system 1230, and the emulated hardware can optionally be different from the hardware illustrated in FIG. 12. In such an embodiment, operating system 1230 can comprise one virtual machine (VM) of multiple VMs hosted at computer 1202. Furthermore, operating system 1230 can provide runtime environments, such as the Java runtime environment or the .NET framework, for applications 1232. Runtime environments are consistent execution environments that allow applications 1232 to run on any operating system that includes the runtime environment. Similarly, operating system 1230 can support containers, and applications 1232 can be in the form of containers, which are lightweight, standalone, executable packages of software that include, e.g., code, runtime, system tools, system libraries and settings for an application.

Further, computer 1202 can be enable with a security module, such as a trusted processing module (TPM). For instance with a TPM, boot components hash next in time boot components, and wait for a match of results to secured values, before loading a next boot component. This process can take place at any layer in the code execution stack of computer 1202, e.g., applied at the application execution level or at the operating system (OS) kernel level, thereby enabling security at any level of code execution.

A user can enter commands and information into the computer 1202 through one or more wired/wireless input devices, e.g., a keyboard 1238, a touch screen 1240, and a pointing device, such as a mouse 1242. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1204 through an input device interface 1244 that can be coupled to the system bus 1208, but can be connected by other interfaces, such as a parallel port, an IEEE 1394 serial port, a game port, a USB port, an IR interface, a BLUETOOTH® interface, etc.

A monitor 1246 or other type of display device can be also connected to the system bus 1208 via an interface, such as a video adapter 1248. In addition to the monitor 1246, a computer typically includes other peripheral output devices (not shown), such as speakers, printers, etc.

The computer 1202 can operate in a networked environment using logical connections via wired and/or wireless communications to one or more remote computers, such as a remote computer(s) 1250. The remote computer(s) 1250 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1252 is illustrated. The logical connections depicted include wired/wireless connectivity to a local area network (LAN) 1254 and/or larger networks, e.g., a wide area network (WAN) 1256. Such LAN and WAN networking environments are commonplace in offices and companies, and facilitate enterprise-wide computer networks, such as intranets, all of which can connect to a global communications network, e.g., the Internet.

When used in a LAN networking environment, the computer 1202 can be connected to the local network 1254 through a wired and/or wireless communication network interface or adapter 1258. The adapter 1258 can facilitate wired or wireless communication to the LAN 1254, which can also include a wireless access point (AP) disposed thereon for communicating with the adapter 1258 in a wireless mode.

When used in a WAN networking environment, the computer 1202 can include a modem 1260 or can be connected to a communications server on the WAN 1256 via other means for establishing communications over the WAN 1256, such as by way of the Internet. The modem 1260, which can be internal or external and a wired or wireless device, can be connected to the system bus 1208 via the input device interface 1244. In a networked environment, program modules depicted relative to the computer 1202 or portions thereof, can be stored in the remote memory/storage device 1252. It will be appreciated that the network connections shown are example and other means of establishing a communications link between the computers can be used.

When used in either a LAN or WAN networking environment, the computer 1202 can access cloud storage systems or other network-based storage systems in addition to, or in place of, external storage devices 1216 as described above, such as but not limited to a network virtual machine providing one or more aspects of storage or processing of information. Generally, a connection between the computer 1202 and a cloud storage system can be established over a LAN 1254 or WAN 1256 e.g., by the adapter 1258 or modem 1260, respectively. Upon connecting the computer 1202 to an associated cloud storage system, the external storage interface 1226 can, with the aid of the adapter 1258 and/or modem 1260, manage storage provided by the cloud storage system as it would other types of external storage. For instance, the external storage interface 1226 can be configured to provide access to cloud storage sources as if those sources were physically connected to the computer 1202.

The computer 1202 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 13:
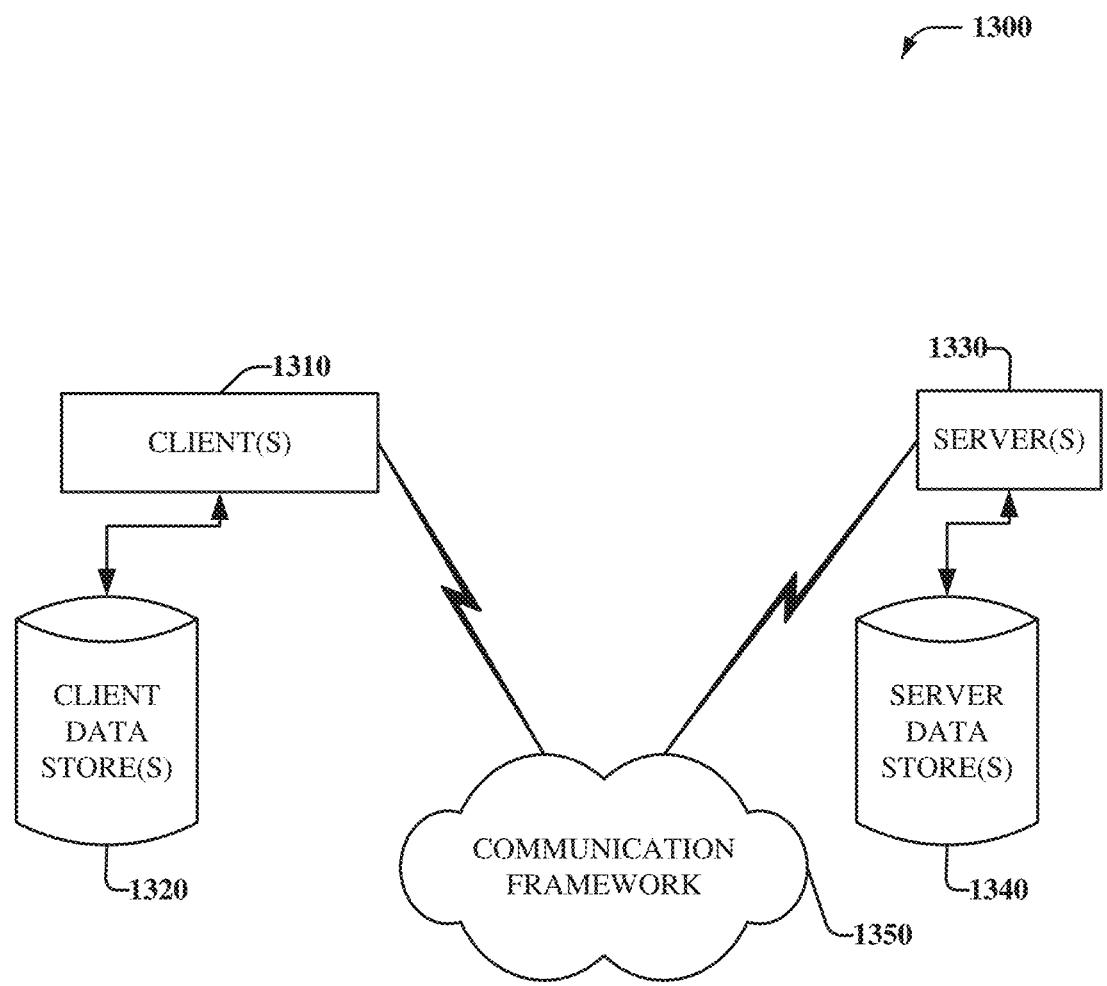
FIG. 13 illustrates an example networking environment operable to execute various implementations described herein.

FIG. 13 is a schematic block diagram of a sample computing environment 1300 with which the disclosed subject matter can interact. The sample computing environment 1300 includes one or more client(s) 1310. The client(s) 1310 can be hardware and/or software (e.g., threads, processes, computing devices). The sample computing environment 1300 also includes one or more server(s) 1330. The server(s) 1330 can also be hardware and/or software (e.g., threads, processes, computing devices). The servers 1330 can house threads to perform transformations by employing one or more embodiments as described herein, for example. One possible communication between a client 1310 and a server 1330 can be in the form of a data packet adapted to be transmitted between two or more computer processes. The sample computing environment 1300 includes a communication framework 1350 that can be employed to facilitate communications between the client(s) 1310 and the server(s) 1330. The client(s) 1310 are operably connected to one or more client data store(s) 1320 that can be employed to store information local to the client(s) 1310. Similarly, the server(s) 1330 are operably connected to one or more server data store(s) 1340 that can be employed to store information local to the servers 1330.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a processor that executes computer-executable components stored in a computer-readable memory, the computer-executable components comprising:
a receiver component that accesses a medical image, wherein the medical image depicts an anatomical structure according to a first medical scanning domain;
a segmentation component that identifies, via execution of a segmentation model, a region-of-interest in the medical image; and
a transformation component that generates, via execution of a machine learning model, a predicted image based on the medical image, wherein the predicted image depicts the anatomical structure according to a second medical scanning domain that is different from the first medical scanning domain, and wherein the transformation component executes the machine learning model on the region-of-interest and does not execute the machine learning model on a remainder of the medical image.

2. The system of claim 1, wherein the first medical scanning domain is a first energy level of a computed tomography (CT) scanning modality, and wherein the second medical scanning domain is a second energy level of the CT scanning modality that is different from the first energy level.

3. The system of claim 1, wherein the first medical scanning domain is a first contrast phase of a computed tomography (CT) scanning modality, and wherein the second medical scanning domain is a second contrast phase of the CT scanning modality that is different from the first contrast phase.

4. The system of claim 1, wherein the computer-executable components further comprise:
a denoise component that applies one or more denoising techniques to the medical image prior to execution of the machine learning model.

5. The system of claim 1, wherein the machine learning model is a deep learning regression model.

6. The system of claim 1, wherein the computer-executable components further comprise:
a training component that trains the machine learning model on a training medical image, wherein the training medical image depicts one or more anatomical structures according to the first medical scanning domain, and wherein the training medical image corresponds to a target annotation image that depicts the one or more anatomical structures according to the second medical scanning domain.

7. The system of claim 6, wherein the training component registers the training medical image with the target annotation image prior to training the machine learning model.

8. A computer-implemented method, comprising:
accessing, by a device operatively coupled to a processor, a medical image, wherein the medical image depicts an anatomical structure according to a first medical scanning domain;
identifying, by the device and via execution of a segmentation model, a region-of-interest in the medical image; and
generating, by the device and via execution of a machine learning model, a predicted image based on the medical image, wherein the predicted image depicts the anatomical structure according to a second medical scanning domain that is different from the first medical scanning domain, and wherein the machine learning model is executed on the region-of-interest and not on a remainder of the medical image.

9. The computer-implemented method of claim 8, wherein the first medical scanning domain is a first energy level of a computed tomography (CT) scanning modality, and wherein the second medical scanning domain is a second energy level of the CT scanning modality that is different from the first energy level.

10. The computer-implemented method of claim 8, wherein the first medical scanning domain is a first contrast phase of a computed tomography (CT) scanning modality, and wherein the second medical scanning domain is a second contrast phase of the CT scanning modality that is different from the first contrast phase.

11. The computer-implemented method of claim 8, further comprising:
applying, by the device, one or more denoising techniques to the medical image prior to execution of the machine learning model.

12. The computer-implemented method of claim 8, wherein the machine learning model is a deep learning regression model.

13. The computer-implemented method of claim 8, further comprising:
training, by the device, the machine learning model on a training medical image, wherein the training medical image depicts one or more anatomical structures according to the first medical scanning domain, and wherein the training medical image corresponds to a target annotation image that depicts the one or more anatomical structures according to the second medical scanning domain.

14. The computer-implemented method of claim 13, further comprising:
registering, by the device, the training medical image with the target annotation image prior to the training.

15. A computer program product for facilitating learning-based domain transformation for medical images, the computer program product comprising a computer-readable memory having program instructions embodied therewith, the program instructions executable by a processor to cause the processor to:
access a medical image, wherein the medical image depicts an anatomical structure according to a first medical scanning domain;
identify, via execution of a segmentation model, a region-of-interest in the medical image; and
generate, via execution of a machine learning model, a predicted image based on the medical image, wherein the predicted image depicts the anatomical structure according to a second medical scanning domain that is different from the first medical scanning domain, and wherein the machine learning model is executed on the region-of-interest and not on a remainder of the medical image.

16. The computer program product of claim 15, wherein the first medical scanning domain is a first energy level of a computed tomography (CT) scanning modality, and wherein the second medical scanning domain is a second energy level of the CT scanning modality that is different from the first energy level.

17. The computer program product of claim 15, wherein the first medical scanning domain is a first contrast phase of a computed tomography (CT) scanning modality, and wherein the second medical scanning domain is a second contrast phase of the CT scanning modality that is different from the first contrast phase.

* * * * *